(12) United States Patent
Mancini

(10) Patent No.: US 9,976,127 B2
(45) Date of Patent: May 22, 2018

(54) MANGANESE SUPEROXIDE DISMUTASE VARIANTS AND USES THEREOF

(71) Applicant: Aldo Mancini, Naples (IT)

(72) Inventor: Aldo Mancini, Naples (IT)

( * ) Notice: Subject to any disclaimer, the term of this patent is extended or adjusted under 35 U.S.C. 154(b) by 0 days. days.

(21) Appl. No.: 15/033,781

(22) PCT Filed: Nov. 3, 2014

(86) PCT No.: PCT/EP2014/073597
§ 371 (c)(1),
(2) Date: May 2, 2016

(87) PCT Pub. No.: WO2015/063306
PCT Pub. Date: May 7, 2015

(65) Prior Publication Data
US 2016/0272949 A1   Sep. 22, 2016

(30) Foreign Application Priority Data

Nov. 4, 2013  (IT) .............................. RM2013A0608
Jul. 25, 2014  (EP) ..................................... 14178505

(51) Int. Cl.
| | | |
|---|---|---|
| A61K 38/44 | (2006.01) | |
| C12N 9/02 | (2006.01) | |
| C12P 21/06 | (2006.01) | |
| C12P 19/34 | (2006.01) | |
| C07H 21/04 | (2006.01) | |
| C07K 1/00 | (2006.01) | |
| A61K 9/00 | (2006.01) | |
| A61K 38/00 | (2006.01) | |

(52) U.S. Cl.
CPC .......... *C12N 9/0089* (2013.01); *A61K 9/0048* (2013.01); *A61K 38/446* (2013.01); *C12Y 115/01001* (2013.01); *A61K 38/00* (2013.01)

(58) Field of Classification Search
CPC .......... C12N 9/0089; C12Y 115/01001; A61K 38/446; A61K 9/0048; A61K 38/00
USPC ..... 424/94.4; 435/189, 69.1, 91.1; 536/23.1, 536/23.2; 530/350
See application file for complete search history.

(56) References Cited

U.S. PATENT DOCUMENTS

| | | | |
|---|---|---|---|
| 7,205,146 B1 * | 4/2007 | Keith ................... | C07K 14/47 435/252.1 |
| 8,460,653 B2 * | 6/2013 | Chen .................... | C12N 9/0089 424/94.4 |
| 2011/0091438 A1 | 4/2011 | Mancini | |

FOREIGN PATENT DOCUMENTS

| | | |
|---|---|---|
| EP | 0284105 A2 | 9/1988 |
| WO | 03072768 A2 | 9/2003 |
| WO | 2008063802 A2 | 5/2008 |

OTHER PUBLICATIONS

Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Mancini et al., "Biophysical and biochemical characterization of a liposarcoma-derived recombinant MnSOD protein acting as an anticancer agent" International Journal of Cancer, 2008, vol. 123, No. 11, pp. 2684-2695.
Mancini et al., "Tumor suppressive activity of a variant isoform of manganese superoxide dismutase released by a human liposarcoma cell line" International Journal of Cancer, 2006, vol. 119, No. 4, pp. 932-943.
Grazia Ruggiero et al., "Effects of a New Human Recombinant MnSOD in the Treatment of Photoaging and Actinic Keratosis", Journal of Cancer Therapy, 2013, vol. 4, No. 6, pp. 56-59.
Kanwar et al.,"Oxidative Damage in the Retinal Mitochondria of Diabetic Mice: Possible Protection by Superoxide Dismutase", Investigative Ophthalmology & Visual Science, 2007, vol. 48, No. 8, pp. 3805-3811.
Kasahara et al., "SOD2 Protects against Oxidation-Induced Apoptosis in Mouse Retinal Pigment Epithelium: Implications for Age-Related Macular Degeneration", Investigative Ophthalmology & Visual Science, 2005, vol. 46, No. 9, pp. 3426-3434.
Borrelli et al., "A recombinant MnSOD is radioprotective for normal cells and radiosensitizing for tumor cells", Free Radical Biology and Medicine, 2008, vol. 46, No. 1, pp. 110-116.
Borrelli et al., "The leader peptide of a human rec. MnSOD as molecular carrier which delivers high amounts of Cisplatin into tumor cells inducing a fast apoptosis in vitro", International Journal of Cancer, 2010, vol. 128, No. 2, pp. 453-359.
Guillaume et al., "Recombinant human manganese superoxide dismutase reduces liver fibrosis and portal pressure in CCl4-cirrhotic rats", Journal of Hepatology, 2012, vol. 58, No. 2, pp. 240-246.
Borrelli et al., "The Functional Role of MnSOD as a Biomarker of Human Diseases and Therapeutic Potential of a New Isoform of a Human Recombinant MnSOD", Biomed Research International, 2014, vol. 7, No. 15, pp. 1149-1160.
Pica et al., "Anti-Cancer, anti-Necrotic and Imaging Tumor Marker role of a novel form of Manganese Superoxide Dismutase and its leader peptide", International Journal of Biology and Biomedical Engineering, 2010, vol. 4, No. 3, pp. 53-60.
International Search Report and Written Opinion for International European Application No. PCT/EP2014/073597. ( dated Mar. 16, 2015) (18 pages).

* cited by examiner

*Primary Examiner* — Ganapathirama Raghu
(74) *Attorney, Agent, or Firm* — Lucas Mercanti, LLP

(57) ABSTRACT

The present invention concerns variant proteins of manganese superoxide dismutase (MnSOD) and uses thereof. In particular, the invention concerns a short variant of recombinant MnSOD, and uses thereof for treating or preventing tumors, as well as for treating or preventing diseases with an etiology relating to an excess of free radicals.

21 Claims, 16 Drawing Sheets

A

B

SEQUENCE LISTING

```
<160> NUMBER OF SEQ ID NOS: 8

<210> SEQ ID NO 1
<211> LENGTH: 693
<212> TYPE: DNA
<213> ORGANISM: Homo sapiens

<400> SEQUENCE: 1
gaattcatgt tgagccgggc agtgtgcggc accagcaggc agctggctcc ggctttgggg      60
tatctgggct ccaggcagaa gcacagcctc cccgacctgc cctacgacta cggcgccctg     120
gaacctcaca tcaacgcgca gatcatgcag ctgcaccaca gcaagcacca cgcggcctac     180
gtgaacaacc tgaacgtcac cgaggagaag taccaggagc gttggccaa gggagatgtt      240 acagcccaga tagctcttca gcctgcactg aagttcaatg gtggtggtca tatcaatcat     300
agcattttct ggacaaacct cagccctaac ggtggtggag aacccaaagg ggagttgctg     360
gaagccatca aacgtgactt tggttccttt gacaagttta aggagaagct gacggctgca     420
tctgttggtg tccaaggctc aggttggggt tggcttggtt tcaataagga acggggacac     480
ttacaaattg ctgcttgtcc aaatcaggat ccactgcaag gaacaacagg ccttattcca     540
ctgctgggga ttgatgtgtg ggagcacgct tactaccttc agtataaaaa tgtcaggcct     600
gattatctaa aagctatttg gaatgtaatc aactgggaga atgtaactga aagatacatg     660
gcttgcaaaa ataagaactc atgttgaaag ctt                                  693

<210> SEQ ID NO 2
<211> LENGTH: 226
<212> TYPE: PRT
<213> ORGANISM: Homo sapiens

<400> SEQUENCE: 2

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
                20                  25                  30

Tyr Asp Tyr Gly Ala Leu Glu Pro His Ile Asn Ala Gln Ile Met Gln
            35                  40                  45

Leu His His Ser Lys His His Ala Ala Tyr Val Asn Asn Leu Asn Val
        50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly His Ile
                85                  90                  95

Asn His Ser Ile Phe Trp Thr Asn Leu Ser Pro Asn Gly Gly Gly Glu
                100                 105                 110

Pro Lys Gly Glu Leu Leu Glu Ala Ile Lys Arg Asp Phe Gly Ser Phe
```

```
            115                 120                 125
Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Asn Lys Asn
    210                 215                 220

Ser Cys
225

<210> SEQ ID NO 3
<211> LENGTH: 639
<212> TYPE: DNA
<213> ORGANISM: Homo sapiens

<400> SEQUENCE: 3
gaattcgcag tgtgcggcac cgggaagcac agcctccccg acctgcccta cgactacggc      60
gccctggaac tcacatcaa cgcgcagatc atgcagctgc accacagcaa gcaccacgcg      120
gcctacgtga caacctgaa cgtcaccgag gagaagtacc aggaggcgtt ggccaaggga      180
gatgttacag cccagatagc tcttcagcct gcactgaagt tcaatggtgg tggtcatatc      240
aatcatagca ttttctggac aaaccctcagc cctaacggtg gtggagaacc caaaggggag      300
ttgctggaag ccatcaaacg tgactttggt tcctttgaca agtttaagga aagctgacg      360 gctgcatctg ttggtgtcca aggctcaggt tggggttggc ttggtttcaa taaggaacgg      420
ggacacttac aaattgctgc ttgtccaaat caggatccac tgcaaggaac aacaggcctt      480
attccactgc tggggattga tgtgtgggag cacgcttact accttcagta taaaaatgtc      540
aggcctgatt atctaaaagc tatttggaat gtaatcaact gggagaatgt aactgaaaga      600
tacatggctt gcaaaaataa gaactcatgt tgaaagctt                             639

<210> SEQ ID NO 4
<211> LENGTH: 208
<212> TYPE: PRT
<213> ORGANISM: Homo sapiens

<400> SEQUENCE: 4

Ala Val Cys Gly Thr Gly Lys His Ser Leu Pro Asp Leu Pro Tyr Asp
1               5                   10                  15

Tyr Gly Ala Leu Glu Pro His Ile Asn Ala Gln Ile Met Gln Leu His
            20                  25                  30

His Ser Lys His His Ala Ala Tyr Val Asn Asn Leu Asn Val Thr Glu
        35                  40                  45

Glu Lys Tyr Gln Glu Ala Leu Ala Lys Gly Asp Val Thr Ala Gln Ile
    50                  55                  60

Ala Leu Gln Pro Ala Leu Lys Phe Asn Gly Gly Gly His Ile Asn His
65                  70                  75                  80

Ser Ile Phe Trp Thr Asn Leu Ser Pro Asn Gly Gly Gly Glu Pro Lys
                85                  90                  95
```

Gly Glu Leu Leu Glu Ala Ile Lys Arg Asp Phe Gly Ser Phe Asp Lys
            100                 105                 110

Phe Lys Glu Lys Leu Thr Ala Ala Ser Val Gly Val Gln Gly Ser Gly
        115                 120                 125

Trp Gly Trp Leu Gly Phe Asn Lys Glu Arg Gly His Leu Gln Ile Ala
    130                 135                 140

Ala Cys Pro Asn Gln Asp Pro Leu Gln Gly Thr Thr Gly Leu Ile Pro
145                 150                 155                 160

Leu Leu Gly Ile Asp Val Trp Glu His Ala Tyr Tyr Leu Gln Tyr Lys
                165                 170                 175

Asn Val Arg Pro Asp Tyr Leu Lys Ala Ile Trp Asn Val Ile Asn Trp
            180                 185                 190

Glu Asn Val Thr Glu Arg Tyr Met Ala Cys Lys Asn Lys Asn Ser Cys
        195                 200                 205

<210> SEQ ID NO 5
<211> LENGTH: 222
<212> TYPE: PRT
<213> ORGANISM: Homo sapiens

<400> SEQUENCE: 5

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 6
<211> LENGTH: 1589
<212> TYPE: DNA
<213> ORGANISM: Homo sapiens

<400> SEQUENCE: 6

```
gcggtgccct tgcggcgcag ctggggtcgc ggccctgctc ccgcgctttt cttaaggccc      60
gcgggcggcg caggagcggc actcgtggct gtggtggctt cggcagcggc ttcagcagat     120
cggcggcatc agcggtagca ccagcactag cagcatgttg agccgggcag tgtgcggcac     180
cagcaggcag ctggctccgg ttttggggta tctgggctcc aggcagaagc acagcctccc     240
cgacctgccc tacgactacg cgccctgga acctcacatc aacgcgcaga tcatgcagct     300
gcaccacagc aagcaccacg cggcctacgt gaacaacctg aacgtcaccg aggagaagta     360
ccaggaggcg ttggccaagg gagatgttac agcccagata gctcttcagc ctgcactgaa     420
gttcaatggt ggtggtcata tcaatcatag cattttctgg acaaacctca gccctaacgg     480
tggtggagaa cccaaagggg agttgctgga agccatcaaa cgtgactttg ttcctttga     540 caagtttaag gagaagctga cggctgcatc tgttggtgtc caaggctcag gttgggttg     600 gcttggtttc aataaggaac ggggacactt acaaattgct gcttgtccaa atcaggatcc     660
actgcaagga acaacaggcc ttattccact gctggggatt gatgtgtggg agcacgctta     720
ctaccttcag tataaaaatg tcaggcctga ttatctaaaa gctatttgga atgtaatcaa     780
ctgggagaat gtaactgaaa gatacatggc ttgcaaaaag taaaccacga tcgttatgct     840
gagtatgtta agctctttat gactgttttt gtagtggtat agagtactgc agaatacagt     900
aagctgctct attgtagcat ttcttgatgt tgcttagtca cttatttcat aaacaactta     960
atgttctgaa taatttctta ctaaacattt tgttattggg caagtgattg aaaatagtaa    1020
atgctttgtg tgattgaatc tgattggaca ttttcttcag agagctaaat tacaattgtc    1080
atttataaaa ccatcaaaaa tattccatcc atatactttg gggacttgta gggatgcctt    1140
tctagtccta ttctattgca gttatagaaa atctagtctt ttgccccagt tacttaaaaa    1200
taaaatatta acactttccc aagggaaaca ctcggctttc tatagaaaat tgcactttt     1260 gtcgagtaat cctctgcagt gatacttctg gtagatgtca cccagtggtt tttgttaggt    1320
caaatgttcc tgtatagttt ttgcaaatag agctgtatac tgtttaaatg tagcaggtga    1380
actgaactgg ggtttgctca cctgcacagt aaaggcaaac ttcaacagca aaactgcaaa    1440
aaggtggttt ttgcagtagg agaaaggagg atgtttattt gcagccaagc aaggagaatt    1500
gggcagctca tgcttgagac ccaatctcca tgatgaccta caagctagag tatttaaagg    1560
cagtggtaaa tttcaggaaa gcagaagtt                                      1589
```

<210> SEQ ID NO 7
<211> LENGTH: 448
<212> TYPE: PRT
<213> ORGANISM: Homo sapiens

<400> SEQUENCE: 7

```
Met Ser Pro Ile Leu Gly Tyr Trp Lys Ile Lys Gly Leu Asp Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95
```

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Met Leu Ser Arg Ala Val Cys Gly Thr Ser Arg Gln Leu Ala
225                 230                 235                 240

Thr Val Leu Gly Tyr Leu Gly Ser Arg Gln Lys His Ser Leu Pro Asp
                245                 250                 255

Leu Pro Tyr Asp Tyr Gly Ala Leu Glu Pro His Ile Asn Ala Gln Ile
            260                 265                 270

Met Gln Leu His His Ser Lys His His Ala Ala Ile Val Asn Asn Leu
        275                 280                 285

Asn Val Thr Glu Glu Lys Tyr Gln Glu Ala Leu Ala Lys Gly Asp Val
    290                 295                 300

Thr Ala Gln Ile Ala Leu Gln Pro Ala Leu Lys Phe Asn Gly Gly Gly
305                 310                 315                 320

His Ile Asn His Pro Ile Phe Trp Thr Asn Leu Ser Pro Asn Gly Gly
                325                 330                 335

Gly Glu Pro Lys Gly Glu Leu Leu Glu Ala Ile Lys Arg Asp Phe Gly
            340                 345                 350

Ser Phe Asp Lys Phe Lys Glu Lys Leu Thr Ala Ala Ser Val Gly Val
        355                 360                 365

Gln Gly Pro Gly Trp Gly Trp Leu Gly Phe Asn Lys Glu Arg Gly His
    370                 375                 380

Leu Gln Ile Ala Ala Cys Pro Asn Gln Asp Pro Leu Gln Gly Thr Thr
385                 390                 395                 400

Gly Leu Ile Pro Leu Leu Gly Ile Asp Val Trp Glu His Ala Tyr Tyr
                405                 410                 415

Leu Gln Tyr Lys Asn Val Arg Pro Asp Tyr Leu Lys Ala Ile Trp Asn
            420                 425                 430

Val Ile Asn Trp Glu Asn Val Thr Glu Arg Tyr Met Ala Cys Lys Lys
        435                 440                 445

<210> SEQ ID NO 8
<211> LENGTH: 198
<212> TYPE: PRT
<213> ORGANISM: Homo sapiens

<400> SEQUENCE: 8

Lys His Ser Leu Pro Asp Leu Pro Tyr Asp Tyr Gly Ala Leu Glu Pro
1               5                   10                  15

His Ile Asn Ala Gln Ile Met Gln Leu His His Ser Lys His His Ala

-continued

```
                 20                  25                  30
Ala Tyr Val Asn Asn Leu Asn Val Thr Glu Glu Lys Tyr Gln Glu Ala
            35                  40                  45

Leu Ala Lys Gly Asp Val Thr Ala Gln Ile Ala Leu Gln Pro Ala Leu
         50                  55                  60

Lys Phe Asn Gly Gly Gly His Ile Asn His Ser Ile Phe Trp Thr Asn
 65              70                  75                  80

Leu Ser Pro Asn Gly Gly Gly Glu Pro Lys Gly Glu Leu Leu Glu Ala
             85                  90                  95

Ile Lys Arg Asp Phe Gly Ser Phe Asp Lys Phe Lys Glu Lys Leu Thr
            100                 105                 110

Ala Ala Ser Val Gly Val Gln Gly Ser Gly Trp Gly Trp Leu Gly Phe
            115                 120                 125

Asn Lys Glu Arg Gly His Leu Gln Ile Ala Ala Cys Pro Asn Gln Asp
            130                 135                 140

Pro Leu Gln Gly Thr Thr Gly Leu Ile Pro Leu Leu Gly Ile Asp Val
145                 150                 155                 160

Trp Glu His Ala Tyr Tyr Leu Gln Tyr Lys Asn Val Arg Pro Asp Tyr
                165                 170                 175

Leu Lys Ala Ile Trp Asn Val Ile Asn Trp Glu Asn Val Thr Glu Arg
            180                 185                 190

Tyr Met Ala Cys Lys Lys
            195
```

MANGANESE SUPEROXIDE DISMUTASE VARIANTS AND USES THEREOF

CROSS-REFERENCE TO RELATED APPLICATIONS

Figure 1:
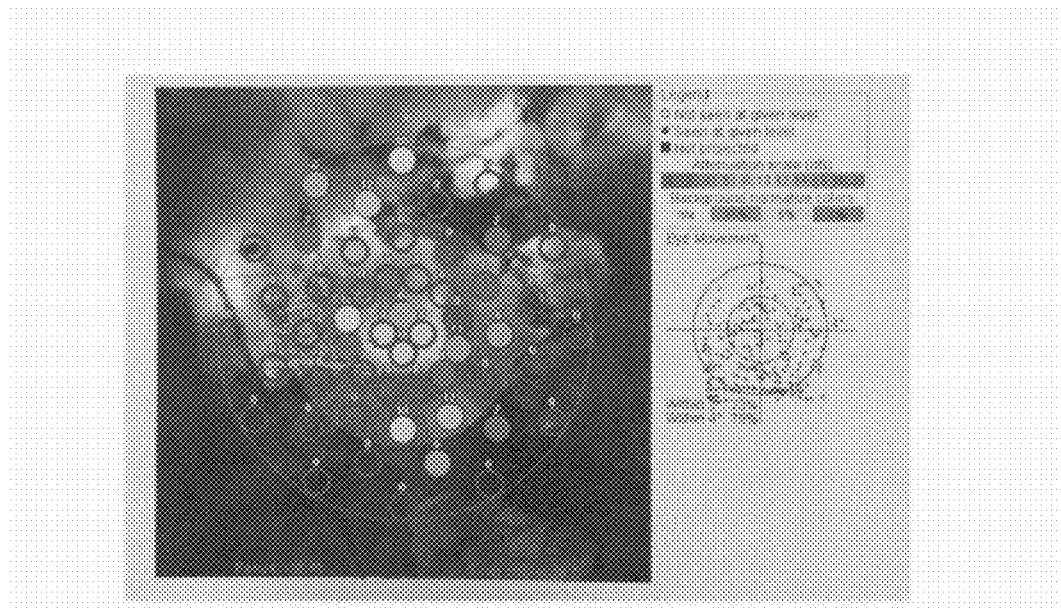

This application is a 371 of PCT/EP2014/073597, filed Nov. 3, 2014, which claims the benefit of both Italian Patent Application No. RM2013A000608 filed Nov. 4, 2013 and European Patent Application 14178505.5 filed Jul. 25, 2014.

FIELD OF THE INVENTION

The present invention concerns variant proteins of Manganese Superoxide Dismutase and uses thereof. In particular, the proteins of the invention have medical and diagnosis applications. In particular, for the treatment and/or prevention of tumors, of disease characterized by an excess of free radicals, of neuroinflammatory diseases.

BACKGROUND ART

A new isoform of MnSOD was recently discovered and isolated from the human liposarcoma cell line (LSA). LSA-type MnSOD differs from wild type human MnSOD by a single threonine to isoleucine substitution at amino acid 82, and its MW (around 30 kDa) is significantly higher than that of conventional MnSOD (24 kDa). Furthermore, unlike wild type MnSOD, which normally remains confined to the mitochondrial matrix (Hunter et al., 1997), LSA-type MnSOD is released from adipocytes into the medium (Mancini et al., 2006). As demonstrated by Mancini et al. (Mancini et al., 2008), recombinant LSA-type MnSOD (rMnSOD) has a distinctive capacity to penetrate and kill cancer cells expressing oestrogen receptors, without having cytotoxic effects on normal cells. The oncotoxic activity of rMnSOD is due to an increase in the level of oxidants both in tumor and leukemic cells, which contain low levels of catalase (Pica et al., 2010).

Leukemia is the most common childhood malignancy worldwide. Extensive evidence has shown that disturbances of oxidative stress metabolism are a common feature of transformed tumor cells (Skarstein et al., 2000). Both alterations of antioxidants and increases in the production of oxygen reactive species play a role in several stages of carcinogenesis (Malyszczak et al., 2005). Radical-mediated DNA damage resulting from the "oxidative damage" incidents leads to arrest or induction of transcription signal transduction pathways, replication errors and genomic instability and represents the first step involved in mutagenesis, carcinogenesis and ageing (Cooke et al., 2003; Valko et al., 2006).

Leukemic cells produce higher amounts of ROS than non-leukemic cells, as they are under a repeated state of oxidative blockade (Al-Gayyar et al., 2007; Battisti et al., 2008). Furthermore, oxidative stress can either inhibit or promote apoptosis, depending on the intensity of the oxidising stimuli. In fact, the apoptosis is induced by moderate oxidising stimuli and necrosis by an intense oxidising effect (Valko et al., 2006). There is evidence that constitutive activation of the MAPK and PI3K pathways occurs frequently in human cancer, possibly due to alteration of genes encoding key components of these pathways or upstream activation of cell-surface receptors resulting from mutations or amplification (Schubert et al., 2007; Courtney et al., 2010). Deregulated signalling due to constitutive activation of these pathways might lead to uncontrolled cell growth and survival, resulting in oncogenic transformation and progression (De Luca et al., 2012).

Superoxide dismutase (SOD) and catalase are among the most efficient enzymatic antioxidants. Three types of SODs are present in human tissues: cytoplasmic Cu/Zn-SOD, extracellular Cu/ZnSOD (ecSOD), and mitochondrial MnSOD (Wann et al., 1994). MnSOD is synthesized in the cytoplasm and then driven into the mitochondrial matrix where it is subsequently cleaved into its mature and enzymatically active form. The data reported on antioxidant enzymes in different human cancer types are controversial. Furthermore, altered levels of antioxidant enzymes (SOD, CAT) and non-enzymatic antioxidants are evident in many human cancer cells (Mc Eligot et al., 2005). It has been shown that SOD and CAT activities are decreased in acute lymphoblastic leukemia (ALL) and chronic lymphocytic leukemia (Oltra et al., 2001). For example, CAT activity is reduced in LLA newly diagnosed patients, in remission induction and remission maintenance patients when compared to healthy subjects (Battisti et al., 2008). SOD expression levels among the various cancer types and stages display heterogeneity which may be related to both different optimal levels of oxidative stress among the various cancer types and the use of alternate pathways in response to oxidative stress.

Recently mitochondrial alterations in cancer cells have been recognized as a target for cancer therapy (Barbosa et al., 2012). In spite of recent progress in therapy, approximately 25% of children and 50% to 70% of adults with T-ALL develop treatment resistant disease (Goldenberg et al., 2003), which carriers a poor prognosis (Bassan et al., 2004). In the present invention, the inventor assessed rMnSOD (long and short form) biological function to determine its oncotoxic effect on pediatric high-risk T-ALL and Jurkat cells and its influence on apoptosis and cellular proliferation mediated by the MAPK and AKT pathway. Medical and diagnostic uses of human MnSOD are indicated in EP 0 284 105, Mancini et al., 2006, WO 03/072768, Ruggiero et al., 2013, WO 2008/063802, Kanwar et al., 2007). However, there is still the need for therapeutic and diagnostic agents based on MnSOD.

DESCRIPTION OF THE INVENTION

The author sequenced the entire cDNA of rMnSOD and observed that the gene sequence coding for the C-terminal portion of rMnSOD at the 3'end, differs in length and sequence from that of the native molecule (MnSOD wild-type or w. type) deposited in the worldwide database (UniProtKB/Swiss-Prot: P04179.1), as shown below.

Amino acid sequence and gene expression of MnSOD w.type (UniProtKB / Swiss-Prot: P04179.1, SEQ ID No. 5)
MLSRAVCGTSRQLAPALGYLGSRQKHSLPDLPYDYGALEPHINAQIMQLH

HSKHHAAYVNNLNVTEEKYQEALAKGDVTAQIALQPALKFNGGGHINHSI

FWTNLSPNGGGEPKGELLEAIKRDFGSFDKFKEKLTAASVGVQGSGWGWL

GFNKERGHLQIAACPNQDPLQGTTGLIPLLGIDVWEHAYYLQYKNVRPDY

LKAIWNVINWENVTERYMACKK

Nucleotide sequence of the MnSOD w.type (Homo sapiens superoxide dismutase 2, mitochondrial (SOD2), nuclear gene encoding mitochondrial protein, transcript variant 1, mRNA NCBI Reference Sequence: NM 000636.2, SEQ ID No. 6)

GCGGTGCCCTTGCGGCGCAGCTGGGGTCGCGGCCCTGCTCCCCGCGCTTT

CTTAAGGCCCGCGGGCGGCGCAGGAGCGGCACTCGTGGCTGTGGTGGCTT

CGGCAGCGGCTTCAGCAGATCGGCGGCATCAGCGGTAGCACCAGCACTAG

CAGCATGTTGAGCCGGGCAGTGTGCGGCACCAGCAGGCAGCTGGCTCCGG

TTTTGGGGTATCTGGGCTCCAGGCAGAAGCACAGCCTCCCCGACCTGCCC

TACGACTACGGCGCCCTGGAACCTCACATCAACGCGCAGATCATGCAGCT

GCACCACAGCAAGCACCACGCGGCCTACGTGAACAACCTGAACGTCACCG

AGGAGAAGTACCAGGAGGCGTTGGCCAAGGGAGATGTTACAGCCCAGATA

GCTCTTCAGCCTGCACTGAAGTTCAATGGTGGTGGTCATATCAATCATAG

CATTTTCTGGACAAACCTCAGCCCTAACGGTGGTGGAGAACCCAAAGGGG

AGTTGCTGGAAGCCATCAAACGTGACTTTGGTTCCTTTGACAAGTTTAAG

GAGAAGCTGACGGCTGCATCTGTTGGTGTCCAAGGCTCAGGTTGGGGTTG

GCTTGGTTTCAATAAGGAACGGGGACACTTACAAATTGCTGCTTGTCCAA

ATCAGGATCCACTGCAAGGAACAACAGGCCTTATTCCACTGCTGGGGATT

GATGTGTGGGAGCACGCTTACTACCTTCAGTATAAAAATGTCAGGCCTGA

TTATCTAAAAGCTATTTGGAATGTAATCAACTGGGAGAATGTAACTGAAA

GATACATGGCTTGCAAAAAGTAAACCACGATCGTTATGCTGAGTATGTTA

AGCTCTTTATGACTGTTTTTGTAGTGGTATAGAGTACTGCAGAATACAGT

AAGCTGCTCTATTGTAGCATTTCTTGATGTTGCTTAGTCACTTATTTCAT

AAACAACTTAATGTTCTGAATAATTTCTTACTAAACATTTTGTTATTGGG

CAAGTGATTGAAAATAGTAAATGCTTTGTGTGATTGAATCTGATTGGACA

TTTTCTTCAGAGAGCTAAATTACAATTGTCATTTATAAAACCATCAAAAA

TATTCCATCCATATACTTTGGGGACTTGTAGGGATGCCTTTCTAGTCCTA

TTCTATTGCAGTTATAGAAAATCTAGTCTTTTGCCCCAGTTACTTAAAAA

TAAAATATTAACACTTTCCCAAGGGAAACACTCGGCTTTCTATAGAAAAT

TGCACTTTTTGTCGAGTAATCCTCTGCAGTGATACTTCTGGTAGATGTCA

CCCAGTGGTTTTGTTAGGTCAAATGTTCCTGTATAGTTTTTGCAAATAG

AGCTGTATACTGTTTAAATGTAGCAGGTGAACTGAACTGGGGTTTGCTCA

CCTGCACAGTAAAGGCAAACTTCAACAGCAAAACTGCAAAAAGGTGGTTT

TTGCAGTAGGAGAAAGGAGGATGTTTATTTGCAGCCAAGCAAGGAGAATT

GGGCAGCTCATGCTTGAGACCCAATCTCCATGATGACCTACAAGCTAGAG

TATTTAAAGGCAGTGGTAAATTTCAGGAAAGCAGAAGTT

In the present invention two synthetic genes were produced, one identified with the acronym sp24-MnSOD_Sint or rMnSOD long form (SEQ ID No. 1) and the corresponding recombinant protein SP24-MnSOD_SINT or rMnSOD long form (SEQ ID No. 2) and another one identified with the acronym rMnSOD short (SEQ ID No. 3) and the corresponding recombinant protein SP6-MnSOD or rMn-SOD short form (SEQ ID No. 4) as follows:

Nucleotide sequence of rMnSOD long form
(SEQ ID NO: 1)
*GAATTC*<u>ATG</u>TTGAGCCGGGCAGTGTGCGGCACCAGCAGGCAGCTGGCTCC <u>GGCTTTGGGGTATCTGGGCTCCAGGCAGA</u>AGCACAGCCTCCCCGACCTGC

CCTACGACTACGGCGCCCTGGAACCTCACATCAACGCGCAGATCATGCAG

CTGCACCACAGCAAGCACCACGCGGCCTACGTGAACAACCTGAACGTCAC

CGAGGAGAAGTACCAGGAGGCGTTGGCCAAGGGAGATGTTACAGCCCAGA

TAGCTCTTCAGCCTGCACTGAAGTTCAATGGTGGTGGTCATATCAATCAT

AGCATTTTCTGGACAAACCTCAGCCCTAACGGTGGTGGAGAACCCAAAGG

GGAGTTGCTGGAAGCCATCAAACGTGACTTTGGTTCCTTTGACAAGTTTA

AGGAGAAGCTGACGGCTGCATCTGTTGGTGTCCAAGGCTCAGGTTGGGGT

TGGCTTGGTTTCAATAAGGAACGGGGACACTTACAAATTGCTGCTTGTCC

AAATCAGGATCCACTGCAAGGAACAACAGGCCTTATTCCACTGCTGGGGA

TTGATGTGTGGGAGCACGCTTACTACCTTCAGTATAAAAATGTCAGGCCT

GATTATCTAAAAGCTATTTGGAATGTAATCAACTGGGAGAATGTAACTGA

AAGATACATGGCTTGCAAAAATAAGAACTCATGTTGAAAGCTT

Amino acid sequence of rMnSOD long form
(SEQ ID NO: 2)
<u>MLSRAVCGTSRQLAPALGYLGSRQ</u>KHSLPDLPYDYGALEPHINAQIMQLH

HSKHHAAYVNNLNVTEEKYQEALAKGDVTAQIALQPALKFNGGGHINHSI

FWTNLSPNGGGEPKGELLEAIKRDFGSFDKFKEKLTAASVGVQGSGWGWL

GFNKERGHLQIAACPNQDPLQGTTGLIPLLGIDVWEHAYYLQYKNVRPDY

LKAIWNVINWENVTERYMACK*NKNSC*

<u>underlined</u>: the sequence of the leader peptide,
*italics*: mutated protein sequence at the C-Term Nucleotide sequence of the short rMnSOD
(SEQ ID No. 3)
*GAATTC*GCAGTGTGCGGCACCGGGAAGCACAGCCTCCCCGACCTGCCCTA

CGACTACGGCGCCCTGGAACCTCACATCAACGCGCAGATCATGCAGCTGC

ACCACAGCAAGCACCACGCGGCCTACGTGAACAACCTGAACGTCACCGAG

GAGAAGTACCAGGAGGCGTTGGCCAAGGGAGATGTTACAGCCCAGATAGC

TCTTCAGCCTGCACTGAAGTTCAATGGTGGTGGTCATATCAATCATAGCA

TTTTCTGGACAAACCTCAGCCCTAACGGTGGTGGAGAACCCAAAGGGGAG

TTGCTGGAAGCCATCAAACGTGACTTTGGTTCCTTTGACAAGTTTAAGGA

GAAGCTGACGGCTGCATCTGTTGGTGTCCAAGGCTCAGGTTGGGGTTGGC

TTGGTTTCAATAAGGAACGGGGACACTTACAAATTGCTGCTTGTCCAAAT

CAGGATCCACTGCAAGGAACAACAGGCCTTATTCCACTGCTGGGGATTGA

TGTGTGGGAGCACGCTTACTACCTTCAGTATAAAAATGTCAGGCCTGATT

ATCTAAAAGCTATTTGGAATGTAATCAACTGGGAGAATGTAACTGAAAGA

TACATGGCTTGCAAAAATAAGAACTCATGTTGAAAGCTT rMnSOD short form amino acid sequence of the protein
(SEQ ID No. 4)
<u>AVCGTG</u>KHSLPDLPYDYGALEPHINAQIMQLHHSKHHAAYVNNLNVTEEK

YQEALAKGDVTAQIALQPALKFNGGGHINHSIFWTNLSPNGGGEPKGELL

EAIKRDFGSFDKFKEKLTAASVGVQGSGWGWLGFNKERGHLQIAACPNQD

-continued

PLQGTTGLIPLLGIDVWEHAYYLQYKNVRPDYLKAIWNVINWENVTERYM

ACK*NKNSC*

Legend: GAATTC: EcoRI restriction site; AAGCTT: HindIII restriction site; ATG: start of the long tale of the protein The enzyme activity, the cytotoxic effect on tumor cells, the ability to internalize into normal and tumor cells and the quantitative dosage of Manganese of the new proteins were examined in comparison with comparative MnSOD.

The SP24-MnSOD_Sint (rMnSOD long form) and SP6-MSOD_SINT (rMnSOD short form) are characterized by:
1. Greater solubility in the majority of the buffers in which it is dissolved compared to the wild-type protein.
2. Improved stability and higher performance of purification after expression in *Escherichia coli*.
3. Higher ability to penetrate cells when compared to other similar proteins (SEQ ID No. 7 and SEQ ID No. 8).

In the present invention, the inventor also tested the effectiveness of the rMnSOD (long and short forms) on leukemic T cells, Jurkat cells, and normal lymphocytes. The results confirm that leukemic T cells can internalize rMn-SOD (long and short forms) and that rMnSOD (long and short forms) causes apoptosis of 99% of leukemic cells without showing toxic effects on healthy cells. Using light and electron microscopy, the inventor determined that an rMnSOD long form concentration of 0.067 µM most effective on apoptosis induction. Western blot analysis showed that treatment with 0.067 µM rMnSOD long form resulted in high expression of the pro-apoptotic protein Bax and low expression of the anti-apoptotic protein Bcl-2 in leukemia cells. Concerning signal transduction pathway no influence was observed after treatment except for Jurkat cells showing a slightly decreased expression of ERK phosphorylation. Author got similar results also with the short form. These results suggest that rMnSOD long or short form may be an effective treatment option for T-cell leukemia, while not being toxic for healthy cells.

The present invention provides a protein encoded by the nucleotide sequence of SEQ ID No. 3 or SEQ ID No. 1, functional variants, derivatives and fragments thereof. Preferably the protein, functional variants, derivatives and fragments thereof is obtainable by a process comprising introducing in a host organism, preferably bacteria, more preferably *E. coli* the nucleotide sequence of SEQ ID No. 3 or SEQ ID No. 1. In a particular embodiment of the invention the protein comprises an amino acid sequence comprised in the following group: SEQ ID No. 4, SEQ ID No. 2, functional variants, derivatives and fragments thereof. In a more particular embodiment the protein, functional variants, derivatives and fragments thereof of the invention comprises a TAG sequence. The functional variants, derivatives and fragments of the proteins comprising or consisting of SEQ ID NO. 2 or SEQ ID NO. 4 of the invention maintain the biological properties and therapeutic effect of the proteins. In the present invention, the terms "mutation" or "derivative" or "variant", as used in the context of the present invention can be understood as substitution, deletion and/or addition of a single amino acid in the target sequence. Preferably, the mutation of the target sequence in the present invention is a substitution. The replacement can be done with a genetically encoded amino acid or an amino acid not genetically encoded. Examples of non-genetically encoded amino acids are homocysteine, hydroxyproline, omithin, hydroxylysine, citrulline, carnitine, etc.

The proteins of the invention have a strong anti-oxidant and anti-inflammatory action and are successfully applied in any circumstance of oxidative imbalance which produces excessive free radicals. The invention refers to the protein, functional variants, derivatives and fragments thereof as above defined for medical and/or diagnostic use, preferably for use in the treatment and/or prevention and/or diagnosis of a disease characterized by an excess of free radicals, as for example vascular disease, including heart, coronary artery or peripheral vascular disease, dilated cardiomyopathy, aneurism, cancer, chronic obstructive pulmonary disease or COPD, dementia, and neurodegenerative disorders, aging, diabetes, autoimmune disorders with rheumatoid arthritis, ocular disease, in particular a disease of the retina or of the crystalline lens, cataract, liver cirrhosis, non-alcoholic steatohepatitis (NASH).

The proteins of the invention are able to preserve transplant organs for a time of over 15 hours in conditions of cold ischemia.

The proteins of the invention allow the recovery of glomerular filtration in organisms that have been treated with cyclosporin-A.

The proteins of the invention reduce by 90% the value of portal hypertension in liver cirrhosis.

The proteins of the invention exert a protection of the eyes exposed to high doses of UV rays, thus preventing cataracts and protecting organisms exposed to sublethal doses of proton rays.

The protein protects against damage caused by an excessive presence of free radicals, in particular in the retina or in dilated cardiomyopathy.

Alternatively, the protein, functional variants, derivatives and fragments as above defined are for use as anti-inflammatory and/or anti-oxidant agent, as for use in the prevention and/or treatment of a neuroinflammatory disease, i.e. neurodegenerative disease, preferably selected from the group consisting of: Alzheimer's disease, Parkinson disease, Multiple Sclerosis, Depression, Basal Ganglia, diseases, Atherosclerosis, Stroke, Trauma, Substance use disorders, Amyotrophic Lateral Sclerosis, and Mitochondrial Encephalopathies.

The proteins of the invention exert a specific and selective cytotoxic activity on cancer cells, in particular leukemia, neuroblastoma, melanoma and breast, ovarian, pancreatic, liver, prostate cancer. The proteins of the invention, for the same reasons, can also be applied clinically as enhancers of other tumor terapies.

Then the protein, functional variants, derivatives and fragments thereof as above defined are for use in the treatment and/or prevention and/or diagnosis of a tumor pathology, preferably the tumor pathology is a leukemia, more preferably acute lymphoblastic leukemia. Alternatively the tumor pathology is a neuroblastoma.

The tumor pathology may affect an adult or a pediatric subject.

In a specific embodiment the protein, functional variants, derivatives and fragments thereof as above defined are for use in the treatment and/or prevention of cataracts.

In a specific embodiment the protein, functional variants, derivatives and fragments thereof as above defined are for use in a radioprotective therapy or prevention of damages, preferably induced by a sublethal dose of proton irradiation.

It is within the scope of the invention a nucleotide sequence coding for the protein as above defined, functional variants, derivatives and fragments thereof; a vector able to efficiently express the protein as above defined, functional variants, derivatives and fragments thereof, comprising said nucleotide sequence. It is also within the scope of the invention a host cell engineered with said vector.

A further embodiment of the invention refers to a pharmaceutical composition comprising the protein, functional variants, derivatives and fragments thereof as above defined, and suitable excipients and/or diluents and/or carriers. In a particular aspect the composition is for ocular administration. The pharmaceutical composition of the present invention can be used for diagnostic or for therapeutic applications.

The exact formulation, mode of administration and dosage can be chosen by the individual G.P. according to the patient's condition. The administration can be done in a single dose or repeatedly in doses at intervals. Dosage and intervals may be adjusted individually in order to provide the therapeutic and/or diagnostic effect, which results in the decrease of symptoms or a prolongation of survival of the patient.

The actual amount of composition administered will, of course, be according to the patient to treat and/or diagnose, to his weight, the severity of illness, the ways of administering and the opinion of the prescribing physician. A suitable daily dosage will be from 0.001 to 10 mg/kg, in particular 0.1 to 5 mg/kg. The administration may be carried out by well-known methods, for example by injection, in particular intravenous, intramuscular, trans-mucosal, subcutaneous or intra-peritoneal injection and/or oral, topical, nasal, inhalation, aerosol and/or rectal application, etc. The administering may be local or systemic. Furthermore, the protein of the invention, variant, derivative or a biologically active fragment of the present invention can be reversibly immobilized and/or adsorbed on the surface and/or inside medical devices or release and vehicular systems of drugs (microspheres). Medical devices and microspheres can be reversibly loaded with the protein of the invention, variant, derivative or a biologically active fragment of this invention, through their binding, impregnation and/or adsorption on the surface of the medical device or of the microsphere or on a level which covers the surface. When the medical device or the microspheres are in contact with biological fluids, the protein of the invention, variant, derivative or a biologically active fragment of it, reversibly immobilized, is released. Therefore, the medical device and the microsphere act as tools that elute the molecule, essence of the present invention, in such a way that their release kinetics can be controlled, ensuring controlled or sustained release, as required by the pharmacological treatment of release. The methods for coating/impregnating the medical devices and loading microspheres are well known by experts of these technologies.

It is essence of the invention, a homologue, a derivative, an equivalent, and a fragment of the protein of the invention.

As used herein, the term "equivalent" means a protein having at least one of the activities of the protein of the invention. "Homologus" shall mean a protein which exerts some changes compared to the protein of the invention. These changes may be a deletion, a truncation, an extension, a chimeric fusion, and/or a mutation. Among the equivalent peptides, those which show more than 80% homology are preferred.

"Derivatives" refers to any peptide, possibly mutated, truncated, and/or extended, which has been chemically modified or contain unusual amino acids. The peptide of the invention, if required, can be modified in vitro and/or in vivo, for example by glycosylation, myristoylation, amidation, carboxylation or phosphorylation, and may be obtained, for example, by synthetic or recombinant techniques known in the field.

As used herein, the term "variants" refers to all types of variants (allelic, mutations ect . . . ) and also includes proteins in different species from the proteins encoded by SEQ ID NO. 1 or 3 in *Homo sapiens*. As an example of these orthologs, one can quote the corresponding proteins in *Mus musculus, Rattus norvegicus, Gallus gallus, Xenopus laevis* and *Danio rerio*.

As used herein, the term "derivative" refers to proteins having a percentage of identity of at least 75% with SEQ ID NO. 1 or with SEQ ID NO. 2, preferably at least 85%, for example at least 90%, and more preferably, at least 95%.

In the present invention, the "fragments" refer to proteins having a length of at least 10 amino acids, preferably at least 15 amino acids, as an example of at least 20 amino acids. In the present invention, all of the fragments and derivatives have the same therapeutic properties of the whole protein.

The term excipients "pharmaceutically acceptable" or "acceptable" refers to molecular entities and compositions that are physiologically tolerable and do not typically produce an allergic reaction, such as gastric upset, dizziness and such, when administered to a human being. Preferably, as used herein, the term "pharmaceutically acceptable" means approved by a regulatory agency. The term "excipient" refers to a diluent, adjuvant, or vehicle with which the compound is administered. Such pharmaceutical carriers can be sterile liquids, such as water and oils, including those of petroleum, animal, vegetable or of synthetic origin, such as peanut oil, soybean oil, mineral oil, sesame oil and such. Salt solutions of water or an aqueous solution and aqueous dextrose and glycerol solutions are preferably employed as carriers, particularly for injectable solutions. Suitable pharmaceutical carriers are described in "Remington's Pharmaceutical Sciences" by E W Martin.

As used herein, the term "nucleotide" refers to RNA or DNA, preferably to DNA. Such DNA may be double-stranded or single-stranded.

Preferably, the nucleotide includes a sequence that encodes the sequence of the protein of the invention.

The nucleotide of the invention might also include the encoding sequence of the peptide previously defined, and an additional coding sequence such as a leader sequence or a sequence of pro-protein, and/or additional non-coding sequences, such as sequences UTR and TAG sequence. As used herein, the term "vector" refers to an expression vector and may for example be in the form of a plasmid, a viral particle, a phage, etc. Such vectors may include bacterial plasmids, phage DNA, baculovirus, yeast plasmids, vectors derived from combinations of plasmids and phage DNA, viral DNA, such as vaccina, adenovirus, pox birds, pseudorabies. A large number of suitable vectors are known to the expert of the field and are available on the market. The following vectors are provided by way of example. Bacterial: pQE70, pQE60, pQE-9 (QIAGEN), PBS, pDIO, phagescript, psiX174, pBluescript SK, pbsks, pNH8A, pNH1 [beta] a, pNH18A, pNH46A (STRATAGENE), ptrc99a, pKK223-3, pKK233-3, pDR540, pRIT5 (Pharmacia). Eukaryotes: pWLNEO, pSV2CAT, pOG44, pXT1, PSG (STRATAGENE), pSVK3, pBPV, pMSG, pSVL (Pharmacia). However, any other vector may be used as long as it is replicable and viable in the host. The polynucleotide sequence, preferably the DNA sequence in the vector is operatively linked to an appropriate expression control sequence (promoter) for direct mRNA synthesis. As examples of such promoters, the inventor could mention a prokaryotic or eukaryotic promoter such as CMV immediate early, HSV thymidine kinase, early and late SV40, LTR retrovirus. The expression vector also contains a ribosome binding site for initial translation and transcription vector. The latter may also include appropriate sequences for amplifying expression.

In addition, the vectors preferably contain one or more selectable marker genes to provide a phenotypic trait for selection of transformed host cells such as di-hydro folate reductase or neomycin resistance for eukaryotic cell culture, or such as tetracycline or ampicillin resistance in E. coli.

As used herein, the term "host cell genetically engineered" relates to host cells that have been transduced, transformed or transfected with the nucleotide or with the vector described previously.

As practical examples of appropriate host cells, the inventor could mention bacterial cells, such as E. coli, Streptomyces, Salmonella typhimurium, fungal cells such as yeast, insect cells such as Sf9, animal cells such as CHO or COS, plant cells, etc., the selection of an appropriate host is considered by experts in the field of application.

Preferably, the host cell above mentioned is an animal cell, and more preferably a human cell. The introduction of nucleotide or of the vector previously described into the host cell can be achieved by well-known method by an expert of the field, such as transfection with calcium phosphate, DEAE—dextran mediated transfection, or electroporation.

The composition of the invention may include one or more additives (for example, stabilizers, preservatives).

According to the present invention, an "effective amount" of a composition or of the peptide of the invention is an amount that is sufficient to achieve the desired biological effect, that is, to penetrate into the cells and release in them whatever chemically had been combined to it. It is understood that the effective dosage will depend on age, sex, health and weight of the patient, kind of concurrent treatment, if any, frequency of treatment, and the nature of the desired effect. The ranges of effective doses provided below are not intended to limit the invention and suggest dose intervals. However, the preferred dosage can be tailored to the individual subject, as understood and determinable by an expert of the field, without undue experimentation. The peptide, nucleotide, vector, and host cell are as described previously.

It within the scope of the invention a kit for the diagnosis of a tumor disease comprising the protein, functional variants, derivatives and fragments thereof as above defined.

FIGURE LEGENDS

The present invention will be illustrated with non-limiting examples in reference to the following figures.

Figure 2:
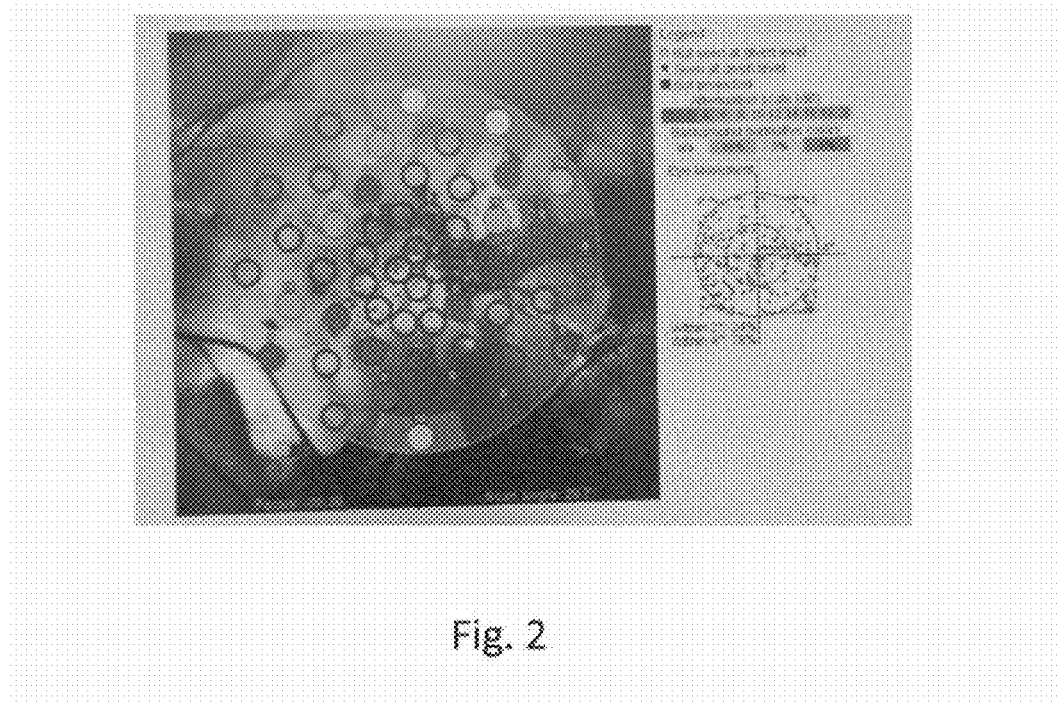

FIG. 1 and FIG. 2: oct microperimetrical examination highlighted in the retina a spot that assesses retinal sensitivity to light stimulus by zone from red 0 to green 16, indicating a good response of the retinal area. For this patient, before treatment there was only one green zone (FIG. 1) and the majority were red zones. After one year of treatment consisting in the administration of 2 eye drops containing rMnSOD long form (100 ug/10 ml) twice a day the green areas were five (FIG. 2). The area of interest is the same as the picture that shows the condition of the patient before treatment. By overlapping the photos, it is possible to observe their perfect match. This demonstrates that it is the same retinal area that is photographed after a lap of time and also demonstrates the proper execution of the examination and its reliability.

Figure 3:
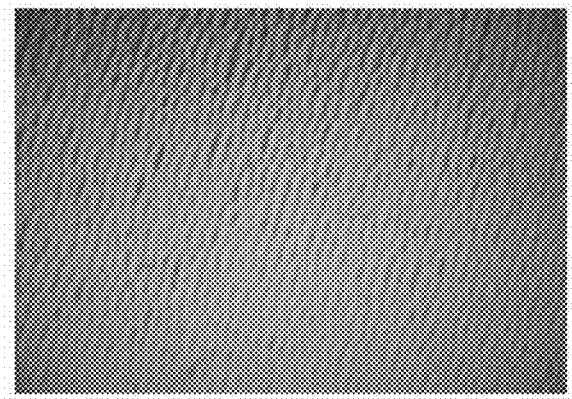
Figure 3:

FIG. 3: (A) Eyes of rabbits exposed to ultraviolet radiation for 60 minutes, treated with the MnSOD long form: the crystallines are structurally intact. (B) Eyes of rabbits exposed to ultraviolet radiation for 60 minutes, treated with comparative MnSOD w.type: the lenses are destroyed.

Figure 4:
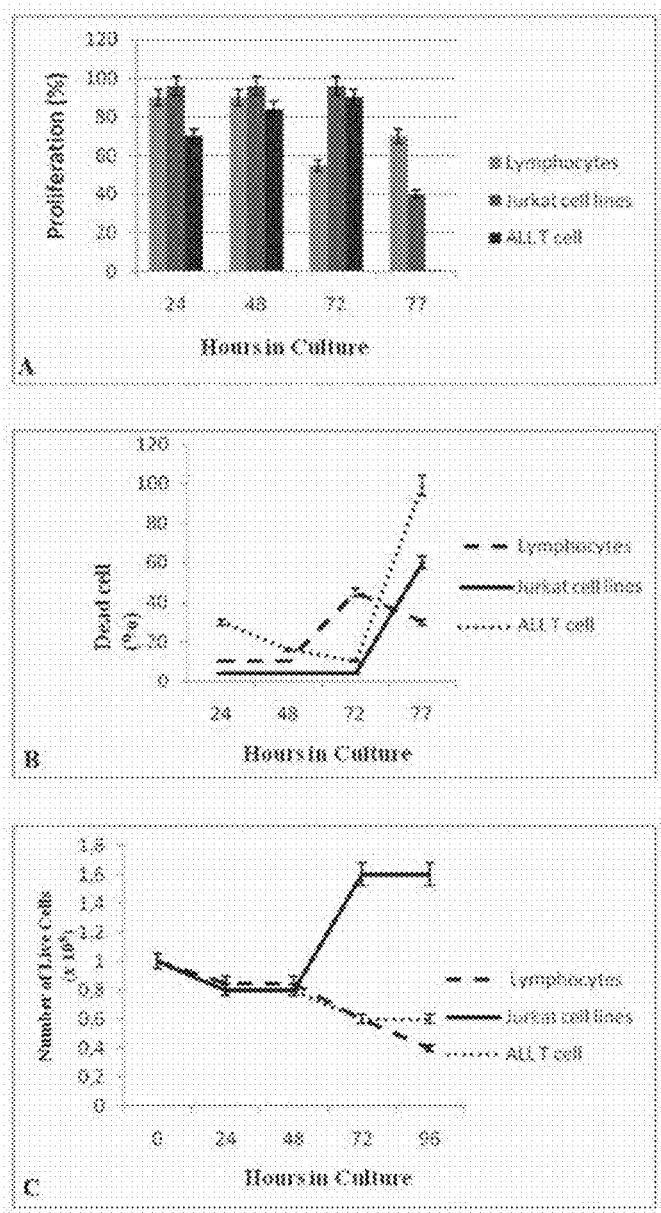

FIG. 4: Proliferation assay and growth inhibition. Survival of T-ALL cells, Jurkat cells and lymphocytes, by using MTT analysis, after 72 hours of growth, and following treatment with 0.067 μM rMnSOD long form for 5 hours. (A) Cell viability by Trypan Blue exclusion assay. Results are the average of three independent experiments.
(B) Spontaneous proliferation curve of Jurkat cells line, T-ALL and lymphocytes after 96 hours of growth.

Figure 5:
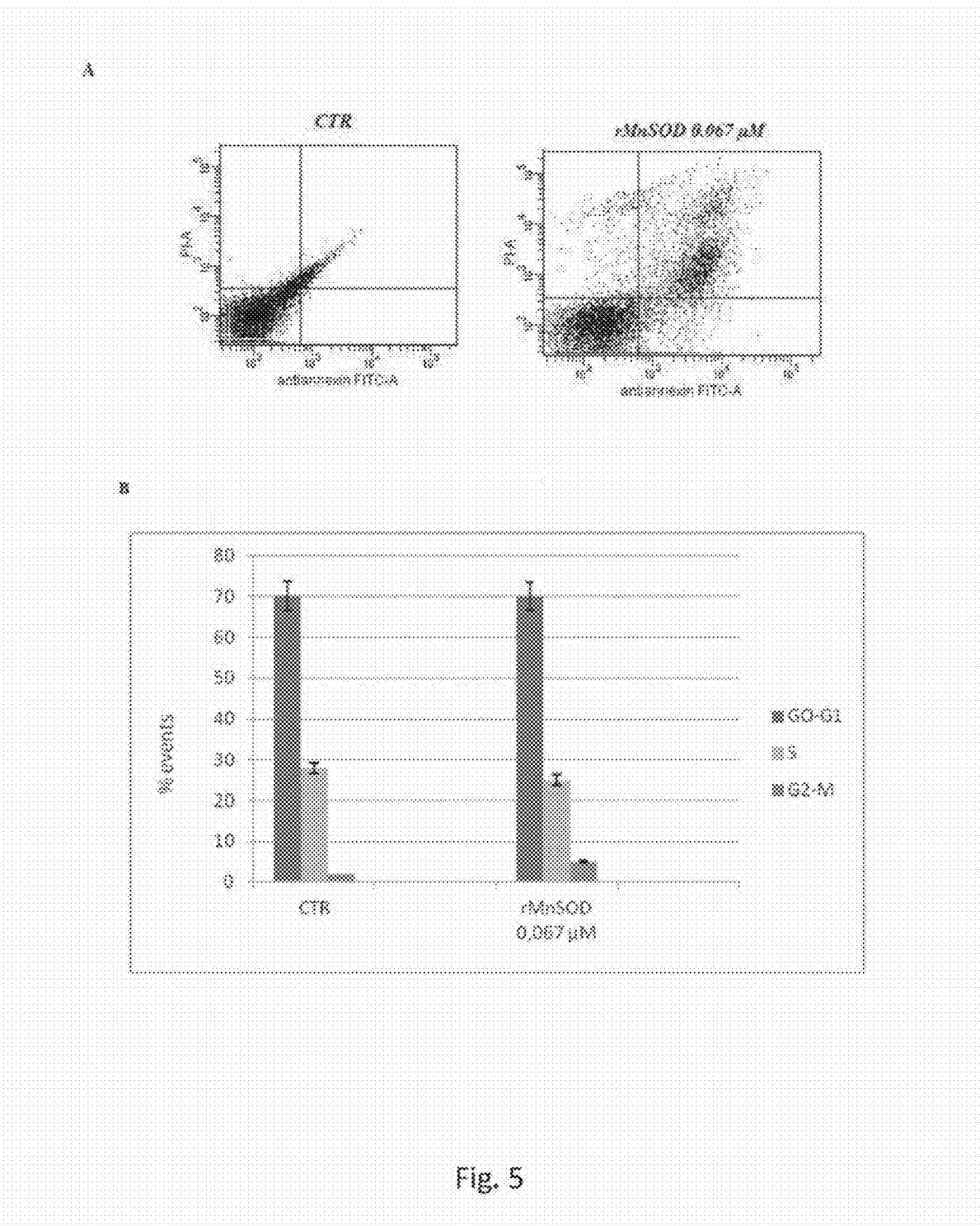

FIG. 5: Effect of rMnSOD long form on apoptosis induction. (A) FACS analysis after double labeling of Jurkat cells with PI and Annexin V following treatment with 0.067 μM rMnSOD long form, compared to the control. (B) Distribution of Jurkat cells in the different phases of the cell cycle after treatment with 0.067 μM rMnSOD long form.

Figure 6:
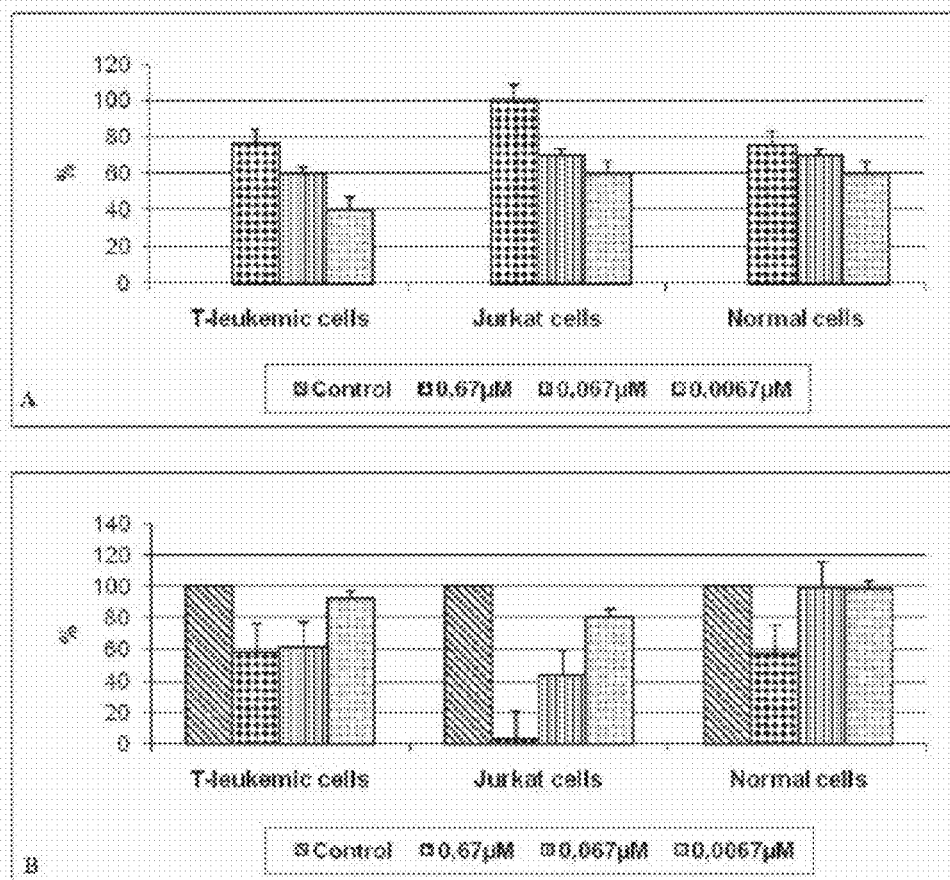

FIG. 6: (A) Percentage of labeled cells at light microscopy. (B) Percentage of labeled cells in Trypan Blue test after the treatments with the different concentrations of rMnSOD long form for 5 hours. The controls displayed no labeling.

Figure 7:
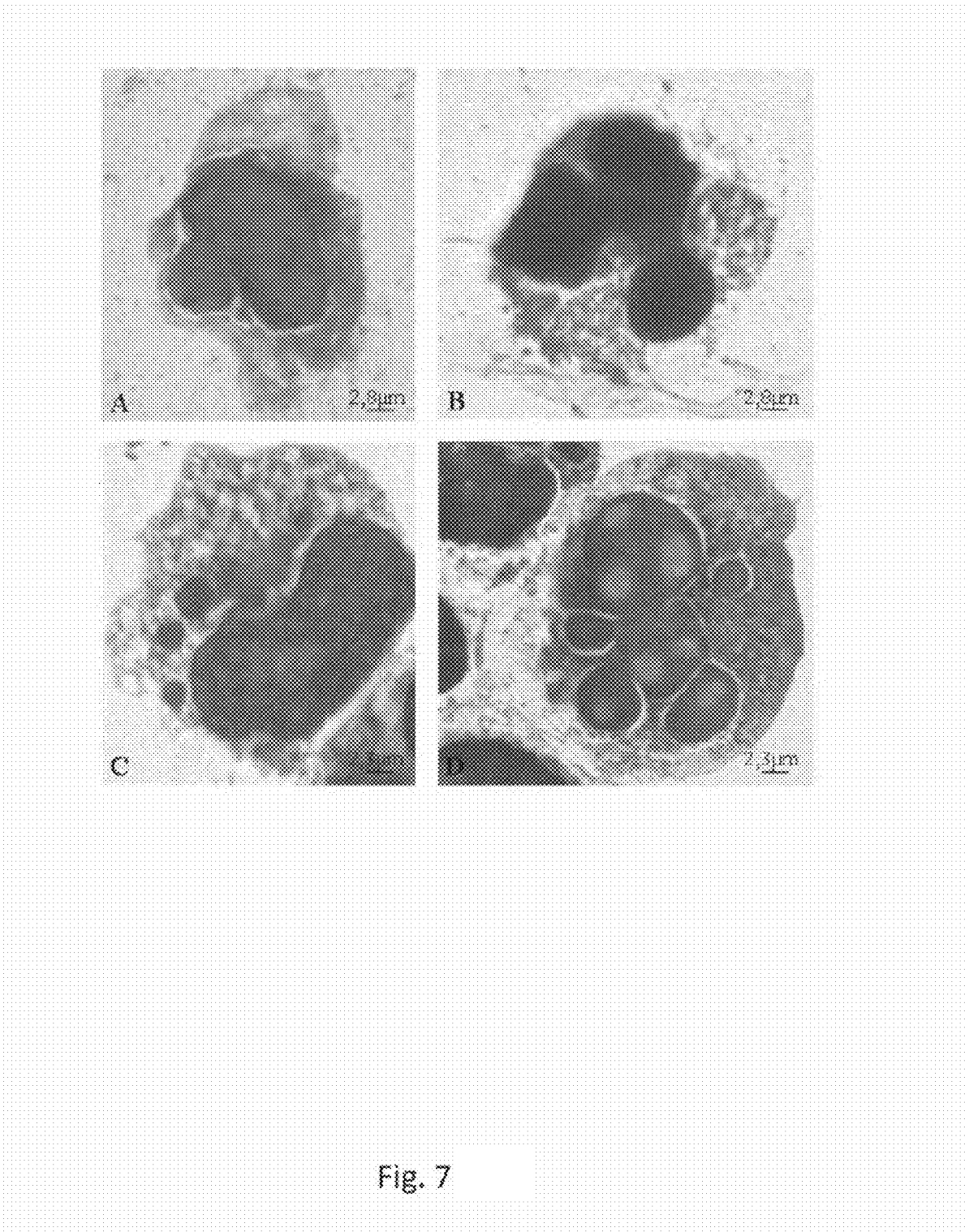
Figure 7:
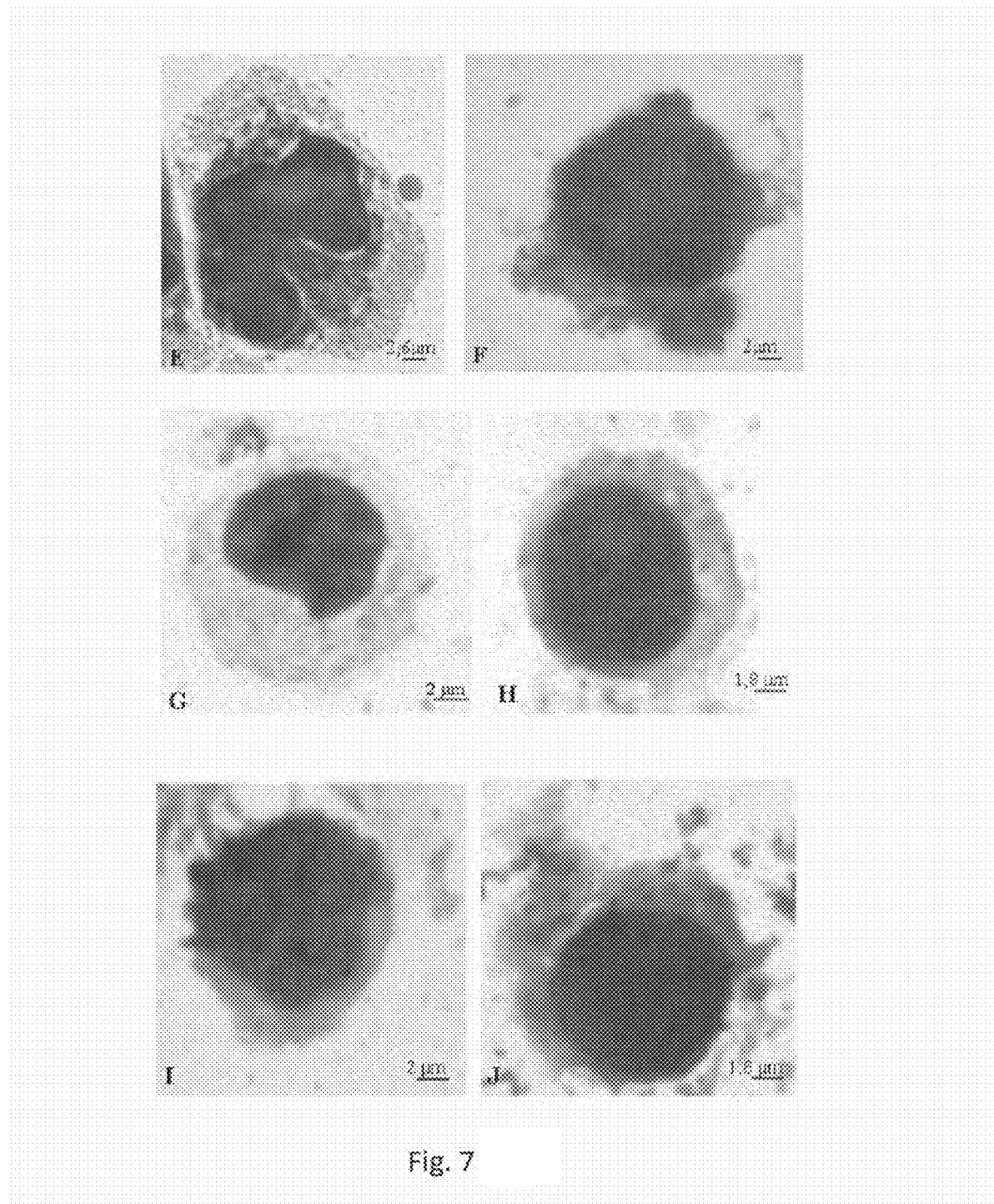

FIG. 7: (A-F) Jurkat cells treated with increasing concentrations of rMnSOD long form. All cells of the panel display an intense brown cytoplasmic and nuclear immunoreaction to anti-rMnSOD, revealed by diaminobenzidine reaction: A) 0.0067 μM rMnSOD long form produces only mild pre-apoptotic changes such initial nuclear and cytoplasmic fragmentations, while 0.067 μM rMnSOD long form (B, C, D, E) lead to a clear and advanced apoptotic fragmentation both a t nuclear and cytoplasmic level and finally 0.67 μM rMnSOD long form (F) is a concentration that, very likely, exceeds the capacity of the cell redox, leading to plasma membrane ruptures.

(G-J) Lymphocytes treated with increasing concentrations of rMnSOD long form. All cells display an intense brown cytoplasmic and nuclear immunoreaction to anti-rMnSOD, revealed by diaminobenzidine reaction: G) control cell; H) and I) cells respectively treated with 0.0067 and 0.067 μM rMnSOD long form, showing a condition of well-being without any signs of apoptosis; J) cell treated with 0.67 μM rMnSOD long form displaying plasma membrane rupture. Very likely, this is a concentration that exceeds the capacity of the cell redox.

Figure 8:
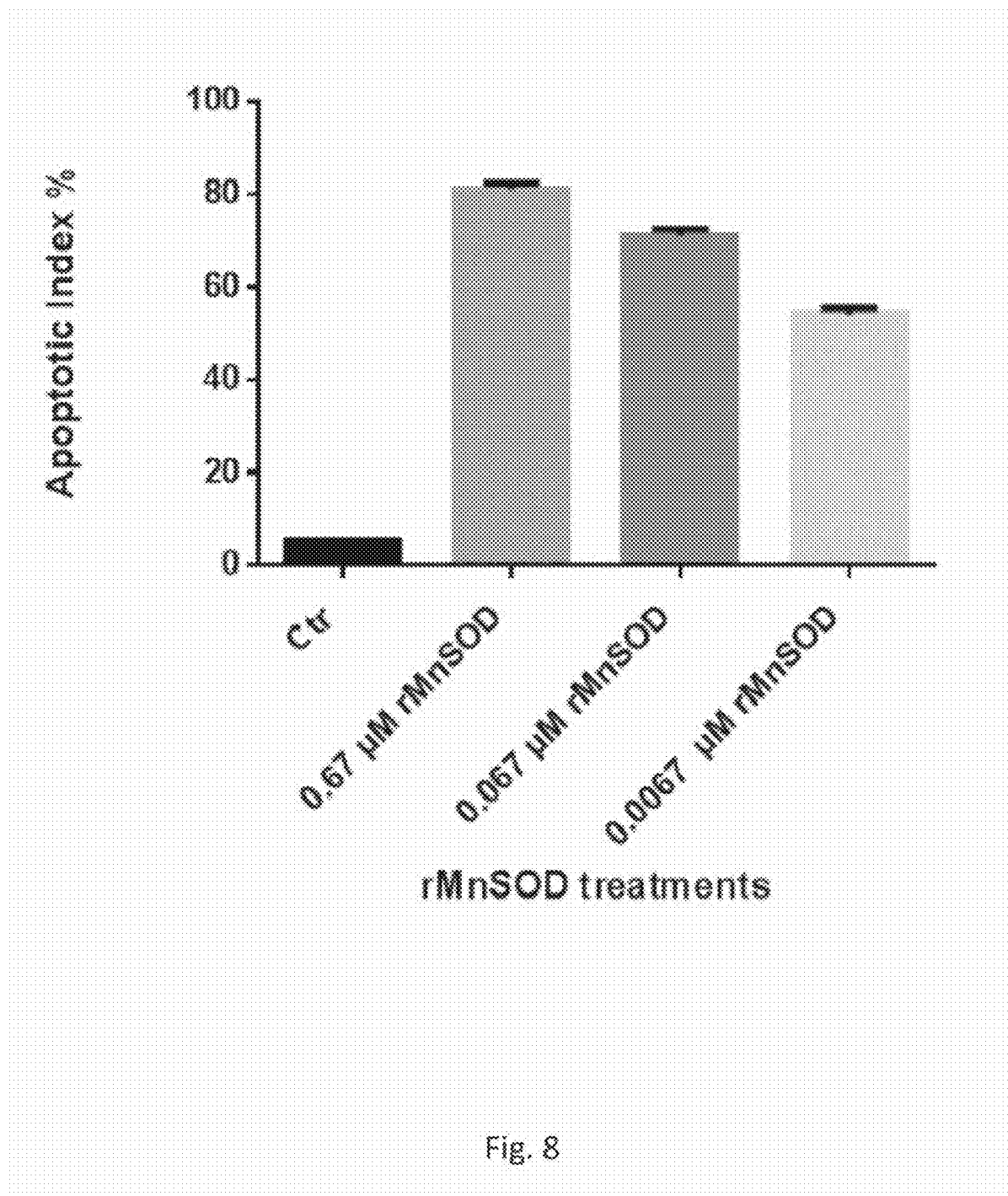

FIG. 8: Apoptotic index. Percentages of apoptotic Jurkat cells following rMnSOD long form treatments.

Figure 9:
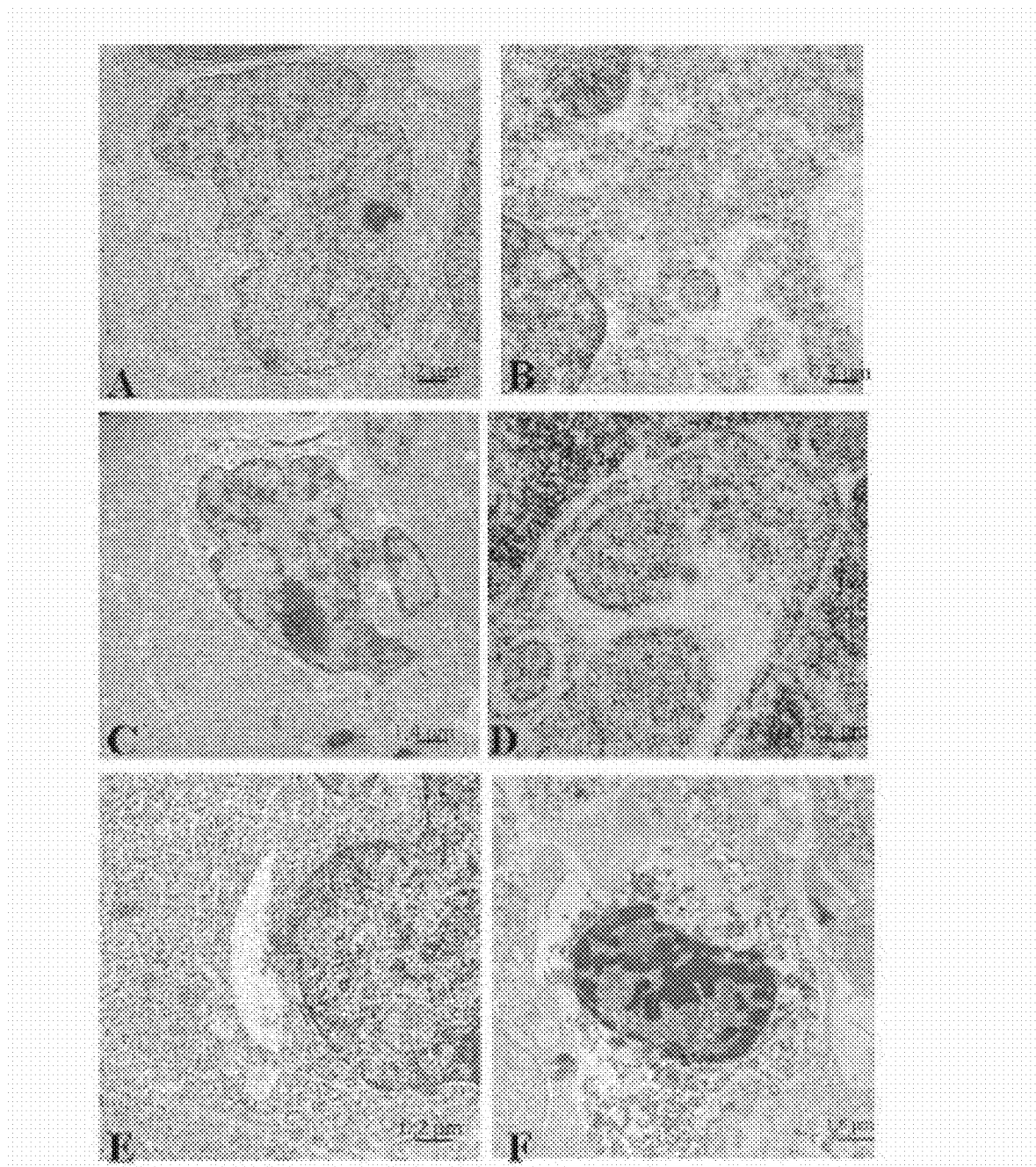
Figure 9:
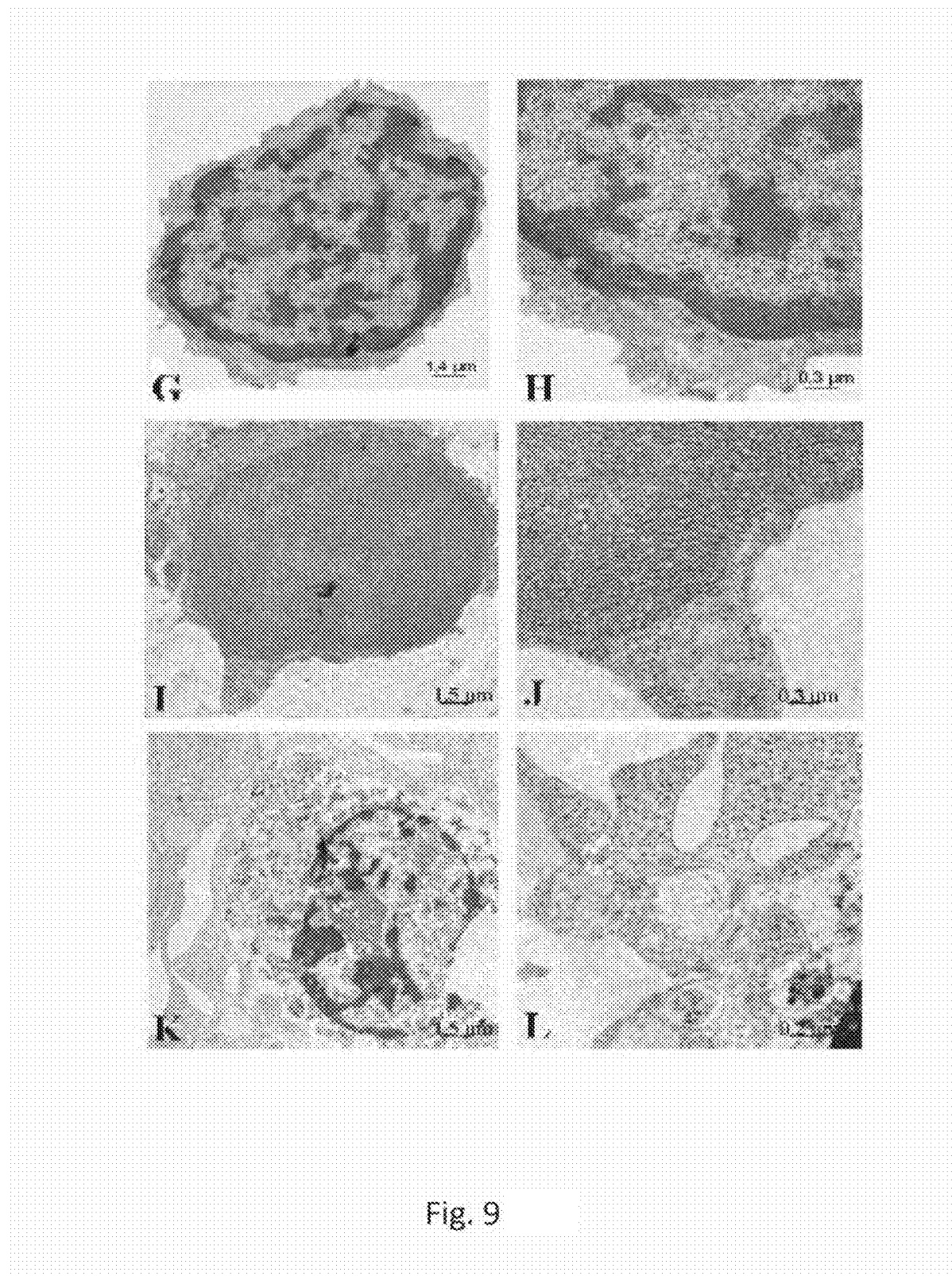

FIG. 9: (A-F) Jurkat cells by TEM following immunoreaction with anti-rMnSOD long form revealed by 15 nm colloidal gold particles: A-B) cell treated with 0.0067 μM rMnSOD long form showing an initial pre-apoptotic nuclear incision and slight cytoplasmic fragmentation; C) and D) cell treated with 0.067 μM rMnSOD long form which lead to a clear nuclear and cytoplasmic apoptotic fragmentations; E-F) cell treated with 0.67 μM rMnSOD, that shows membrane rupture. (G-L) Lymphocytes treated with increasing concentrations of rMnSOD long form respectively followed by immune-revealing with anti-rMnSOD long form and 15 nm colloidal gold particles. G) and H) Control cells; I) and J) lymphocytes treated with 0.067 μM rMnSOD long form displaying a well-being condition while in K) and L) lymphocytes treated with 0.67 μM rMnSOD long form show cell damage.

Figure 10:
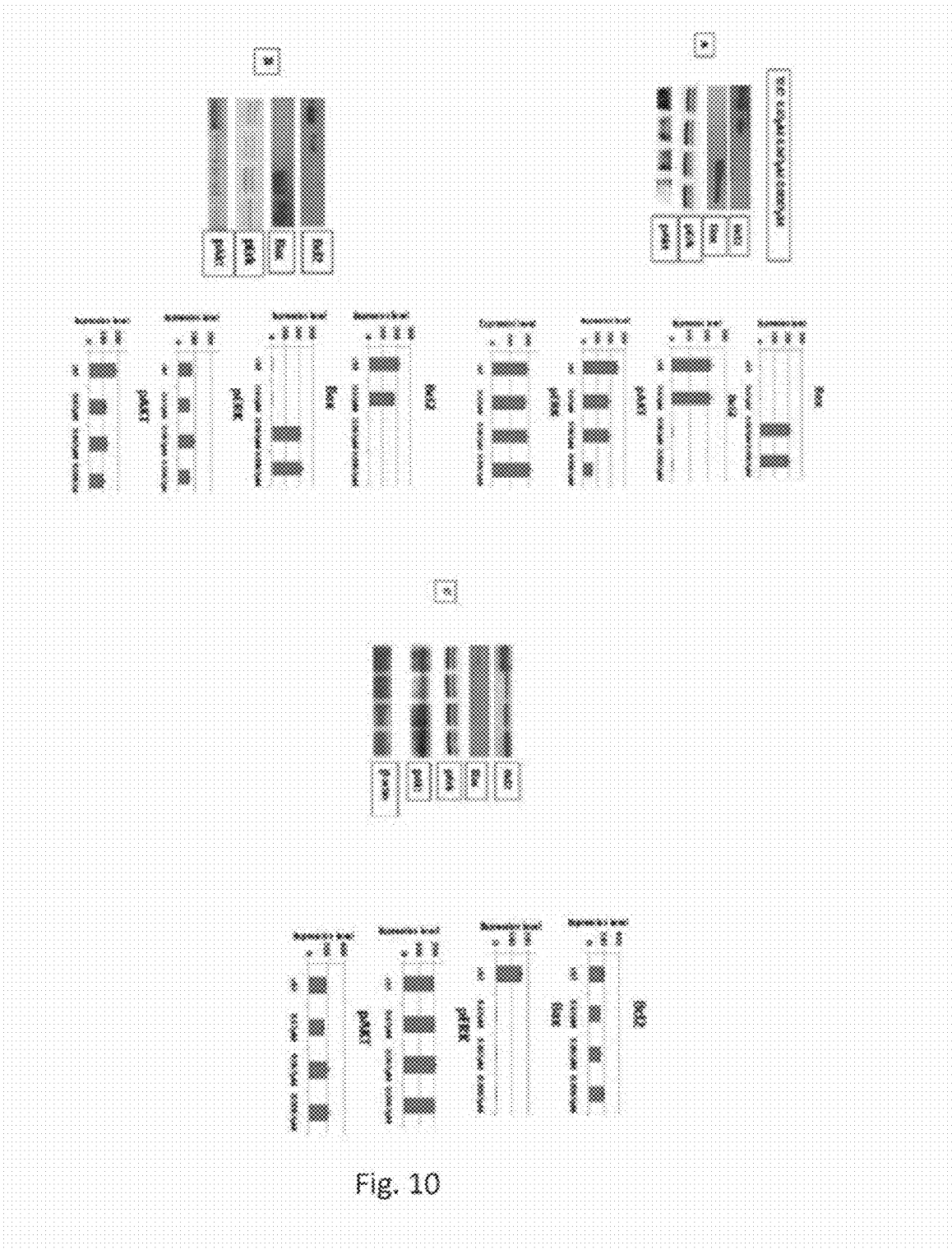

FIG. 10: Western Blot Assay and software analysis of proteins expression: T-ALL cells (A), Jurkat cell line (B) and lymphocytes (C) were processed for the determination of Bcl-2, Bax, the phosphorylation of ERK and AKT after rMnSOD long form treatment at a final concentration ranging from 0.0067 to 0.67 μM. The experiments were performed at least three different times and the results were always similar. UC: untreated cells. Scan of the bands associated with expression of Bcl-2, Bax, pERK and pAKT in T-ALL (D), Jurkat (E) and lymphocytes (F) normalized with the house-keeping protein, was performed with a dedicated software and the intensities of the bands were expressed as arbitrary units (%, mean of three different experiments).

Figure 11:
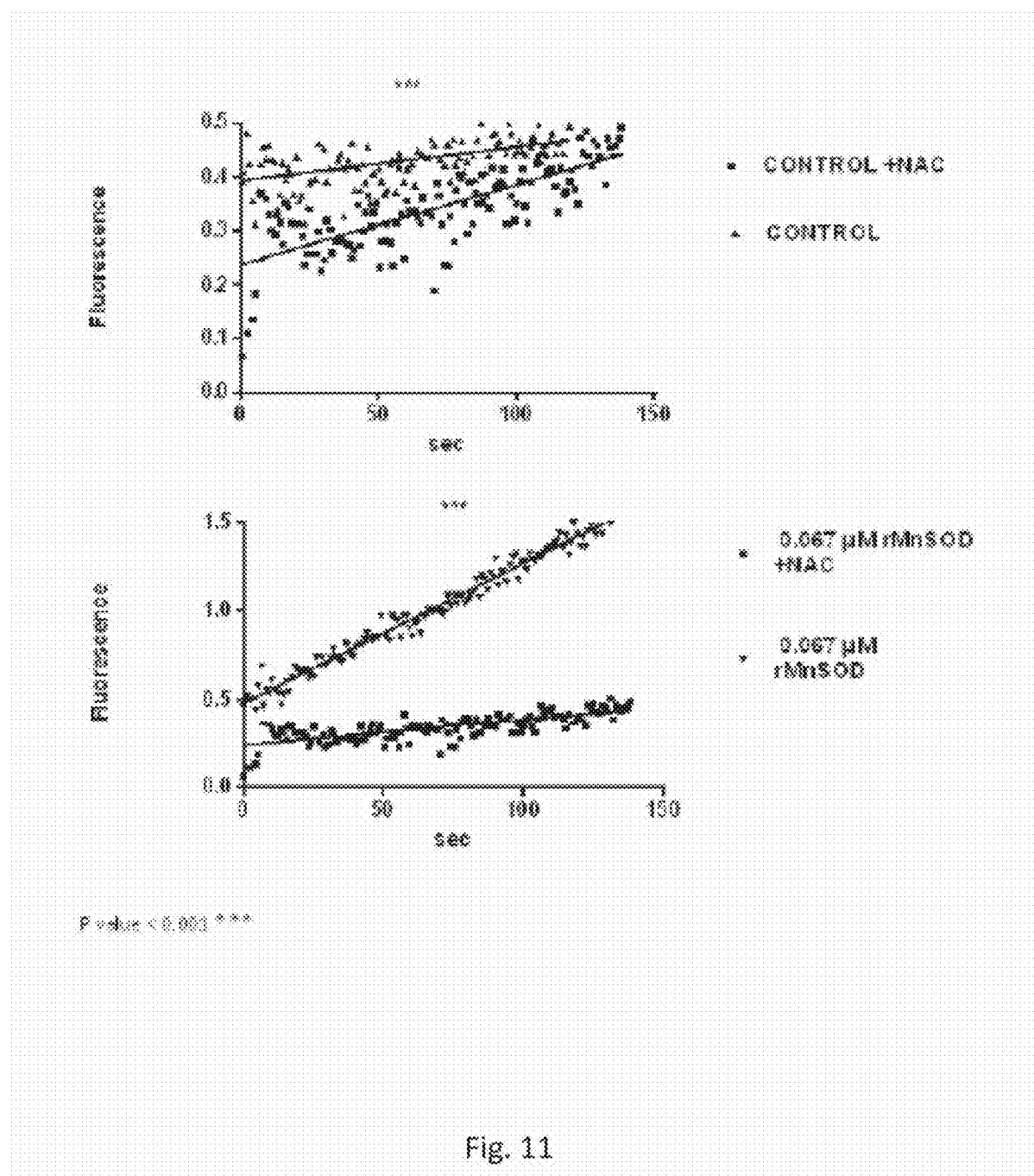

FIG. 11: Spectrofluorimetric analysis of reactive oxygen species. (A) Control Jurkat cells treated with or without NAC. (B) Jurkat cells pre-incubated with or without NAC and then with rMnSOD long form. Results are the means of three experiments.

Figure 12:
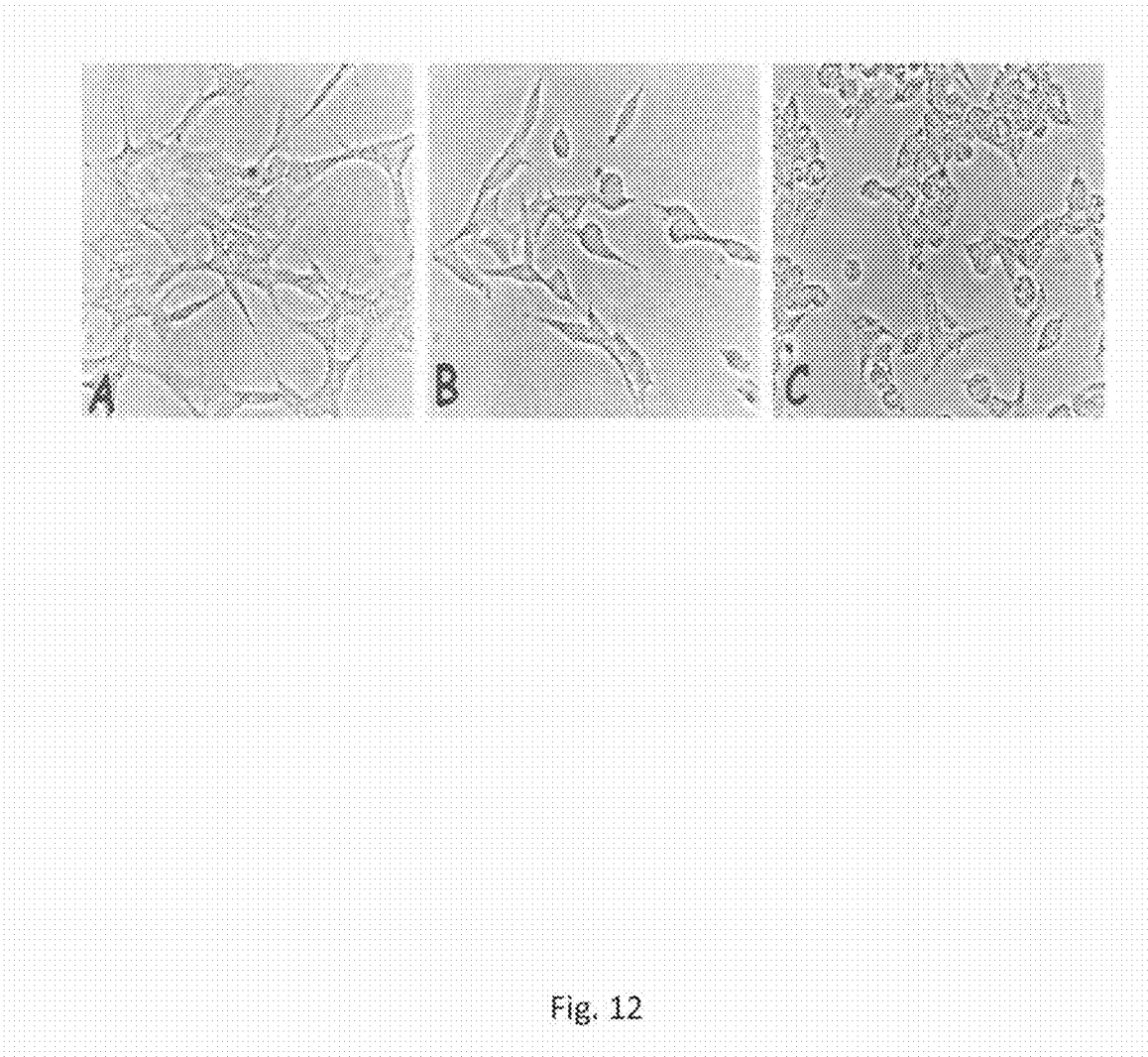

FIG. 12: The effect of rMnSOD long form was investigated by an in vitro model of cell culture (Neuroblastoma SK-N-BE cell line). The recombinant protein was rapidly internalized by neuron-like cells with sign of toxicity after 5-6 hr in culture. Pictures show an altered cellular morphology after rMnSOD long form treatment. A) Untreated cells; B) Cells administered with rMnSOD long form, after 1 h, show round shapes due to retraction of cytoplasm in comparison with control cultures (A); C) Cells exposed to rMnSOD long form show ongoing cell death features after 6 h treatment; Phase-contrast microscopy 40× magnification.

Figure 13:
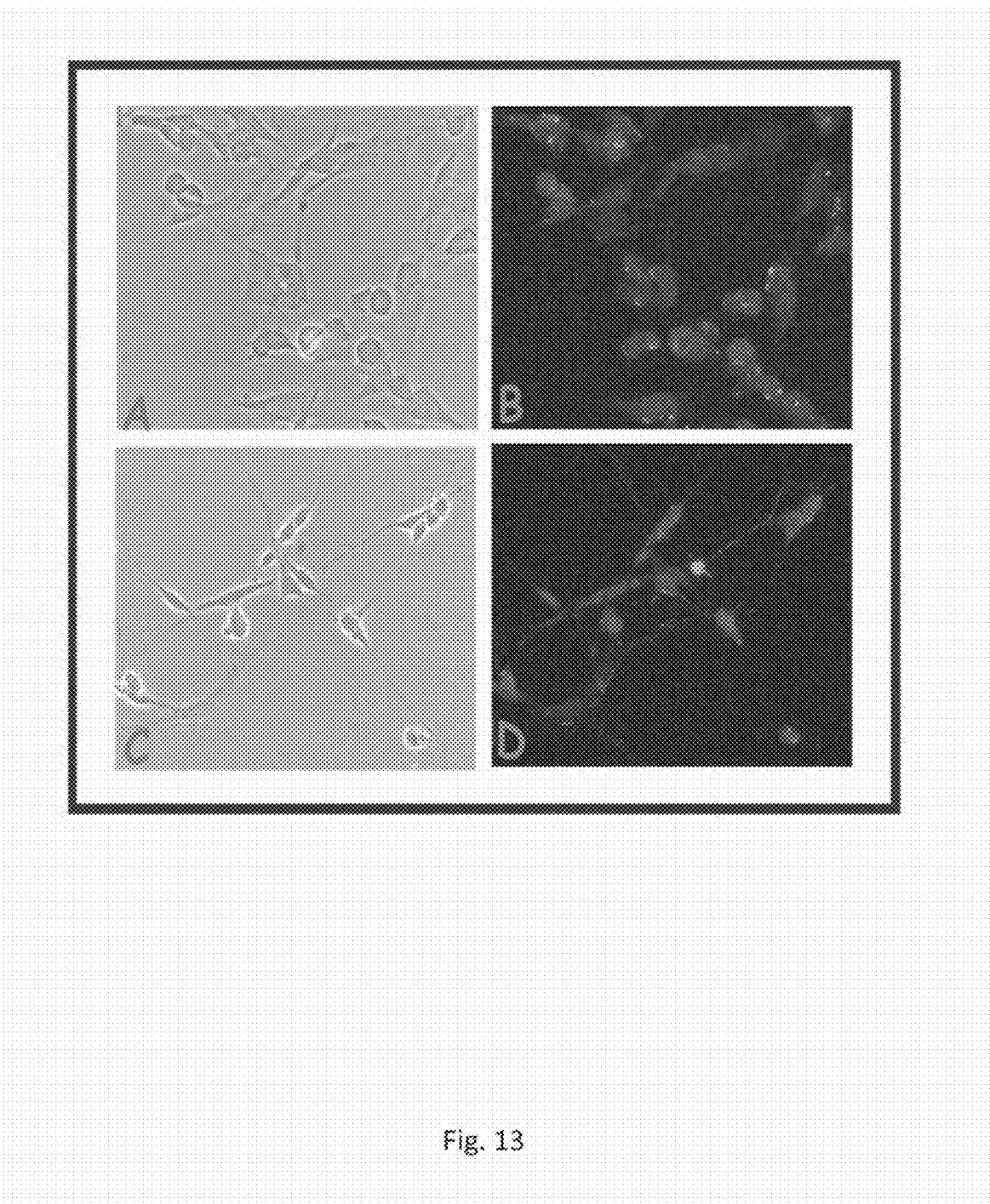

FIG. 13: rMnSOD long form is internalised by undifferentiated and differentiated SK-N-BE after 1 h of treatment. Pictures show the intracellular localization of the recombinant protein immunostained with anti-rMnSOD long form polyclonal antibody. rMnSOD long form is in green, nuclei are blue. A) and B) Undifferentiated cells; C) and D) Differentiated cells; phase-contrast microscopy (A, C); fluorescent microscopy (B, D); 40× magnification.

Figure 14:
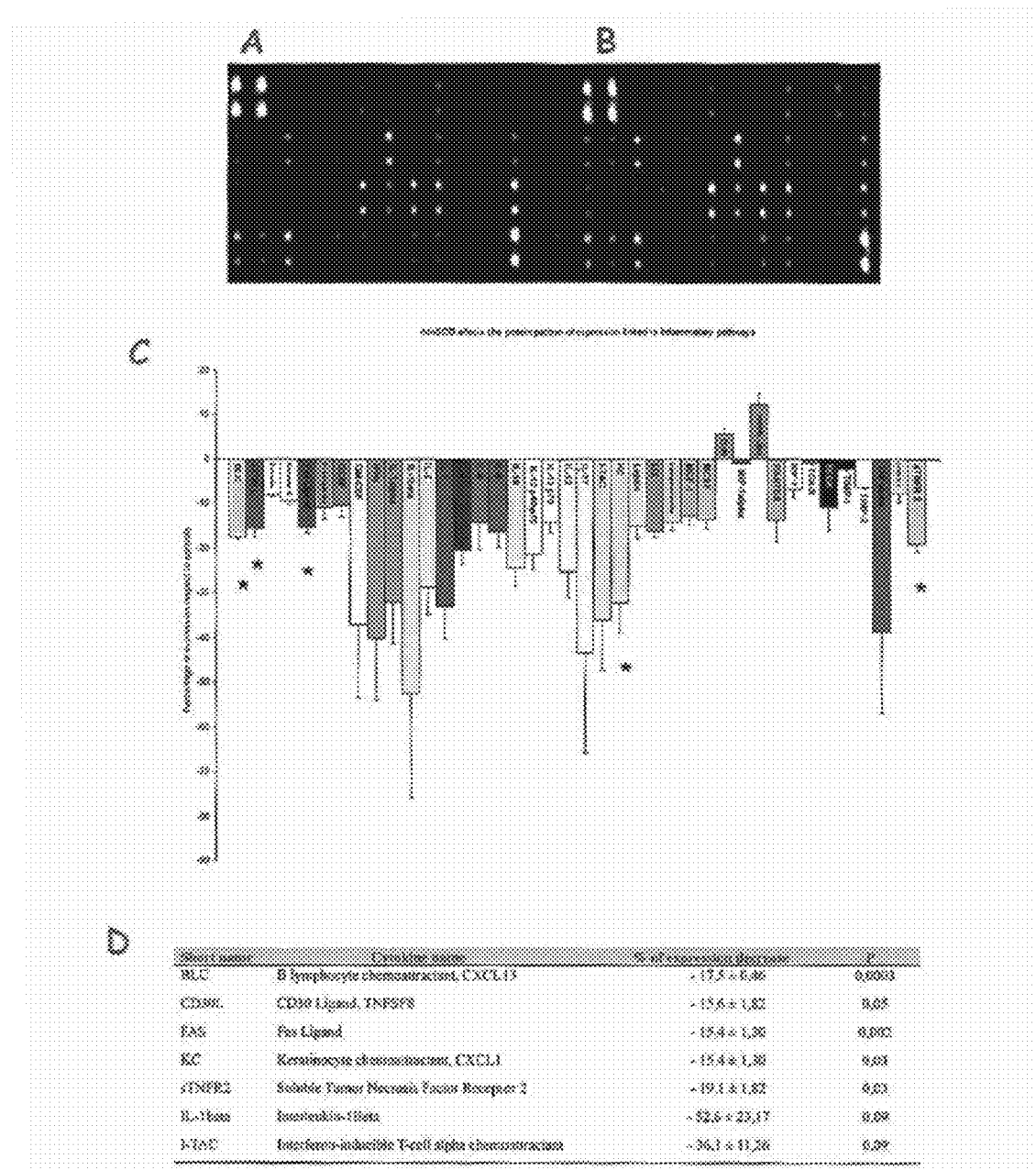

FIG. 14: rMnSOD long form administration modulates cytokines expression in brain cortex. A) Simultaneous detection of multiple cytochines by the Abcam Membrane Antibody Array provides a powerful tool to screen inflammatory factors unravelling the role of individual factors in physiologic or pathologic processes. The membranes were probed with brain cortex homogenates dissected from rMnSOD long form treated and control mice. B) The Graph represents the comparison of the percentage of expression of 40 inflammatory factors detected in test vs untreated samples (n=8). The picture shows a wide down-regulation of the inflammatory proteins in rMnSOD long form treated mice with significant decrease of 4 cytokines (red bars) listed in the table (C). Moreover, 4 proteins showed a trend of expression decrease borderline of reaching any statistical significance (green bar): Only one protein shows a slight, not statistically significant tendency to increase after rMnSOD long form treatment (C). (D) summary table of the results.

Figure 15:
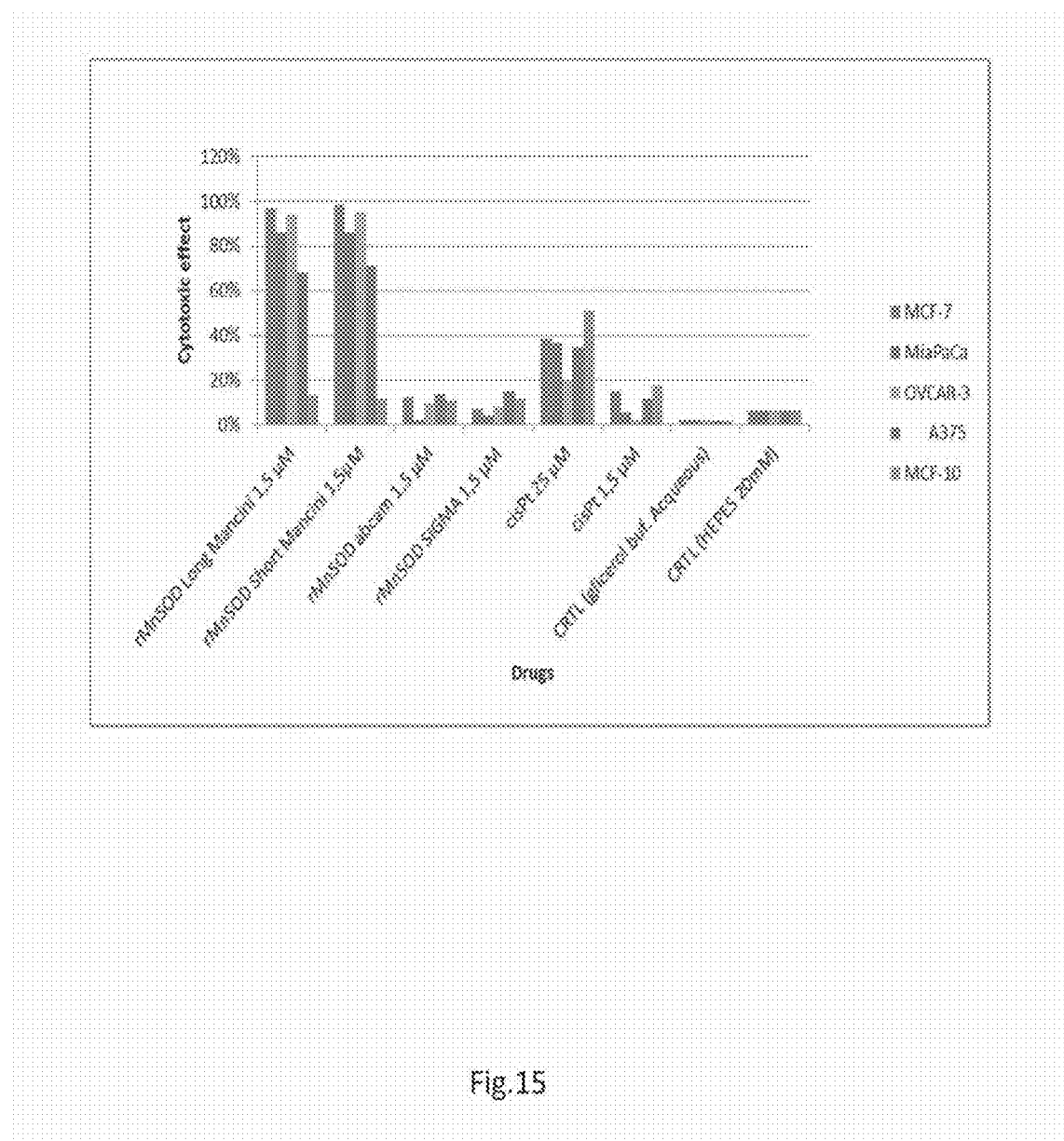

FIG. 15: LDH release into the culture supernatant, expressed as percent of total LDH (from cell lysis induced by detergent treatment). Approximately 3% LDH was found in the medium of untreated cultures. rMnSODs were tested for their cytostatic and cytolytic effects on other human mammary epithelial cell lines of normal (MCF-10) or tumor (MCF-7) origin and on a variety of non mammary transformed cells (OVCAR-3, MiaPaCa, A-375). rMnSOD long form Mancini induced MCF-7 cell culture to release 97% of their LDH content into medium (as compared to the artificial LDH-release induced by detergent treatment), whereas very lower increase in LDH activity could be detected in MCF-10 cell culture supernatants upon application of this recombinant protein versus 12.20% of comparative rMnSOD (Abcam) and 7.30% of comparative rMnSOD (Sigma). The tumor-derived MIA PaCa-2, OVCAR-3, A375 cells all showed a striking sensitivity to rMnSOD long form Mancini-induced killing.

EXAMPLE 1: PRODUCTION OF SP24-MNSOD_SINT (RMNSOD LONG FORM) AND SP6-MNSOD_SINT (RMNSOD SHORT FORM)

Two recombinant synthetic proteins were prepared. The first carrying the leader peptide of 24 aa, the second one, carries, the leader peptide composed of 6 aa. Both proteins exert the same effect/function.

Protocol of Production and Purification of Recombinant Protein rMnSOD Short (Coding Sequence of 639 bp) and rMnSOD Long (Coding Sequence of 693 bp).

Two different nucleotide sequences encoding the rMnSOD, different in the length of the N-terminal end of the protein, respectively rMnSOD short (639 bp) and rMnSOD long (693 bp) were cloned into the expression vector pET21a+(Novagen) using the restriction sites EcoRI to 5'HindIII and 3'. Specifically the two synthesized gene sequences are SEQ ID NO: 1 for the nucleotide sequence of rMnSOD long (amino acid sequence of rMnSOD long is SEQ ID NO: 2) and SEQ ID No. 3 for the nucleotide sequence of the short rMnSOD (amino acid sequence of rMnSOD short is SEQ ID No. 4).

The resulting recombinant constructs (pET21a+_rMnSOD short and pET21a+rMnSOD long) have been transformed into BL21 cells (Novagen) according to the protocol provided by the manufacturer.

The cells transformed with each of the constructs were inoculated in LB medium (Luria-Bertani) supplemented with Ampicillin (100 mg/ml) in flasks incubated at 37° C. under stirring until reaching an optical density of between 0.4-0.8 OD/ml.

The expression of each of the recombinant proteins was induced by addition of 0.1 mm IPTG (Isopropyl-β-D-1-thiogalactopyranoside) incubating the culture at 25° C. under stirring. After 4 hr of growth, the culture is stopped and the cells separated from the culture medium by centrifugation.

The cell pellets are re-suspended in T7•Tag Bind/Wash Buffer (provided by the kit purification T7•Tag® Affinity Purification Kit, Novagen) and subjected to sonication.

The cell lysate was then loaded onto a column T7•Tag Antibody Agarose (provided by the kit purification T7•Tag® Affinity Purification Kit, Novagen) and purified according to the specifications given by the manufacturer.

The solution containing the purified protein is sterilized by filtration in sterility with filters with cutoff of 0.22 μm. The wild-type SOD bovine protein was purchased from SIGMA (code S 969715KU).

EXAMPLE 2: CYTOTOXIC EFFECT OF SYNTHETIC SP24-MNSOD ON HUMAN TUMOR CELLS IN CONTINUOUS CULTURE, AS ASSESSED BY LDH RELEASE FROM TUMOR CELLS AFTER INCUBATION WITH THE PROTEIN OF THE PRESENT INVENTION

Materials and Methods

Cells

The cells used for the assessment of the cytotoxic activity of the recombinant protein derived from the synthetic gene are the following and have been obtained from the sources indicated below.

MCF-7 cells (human breast carcinoma) from ATCC HTB-22™, A-2780 (human ovarian carcinoma cells) from the European Collection of Cell Cultures (ECACC, Salisbury, Wiltshire, UK), Huh7 (human hepatoma cells by JCRB043

NIBIO JCRB Cell Bank, National Institute of Biomedical Innovation), DU145 (cells of human prostate cancer) from ATCC HTB 81 and finally the A375 (human melanoma cells) from the ATCC CRL 1619™, MiaPaCa-2 (ATCC-CRL-1420™, OVCAR-3 (ATCC-HTB-161), MCF-10 (ATCC-CRL-10317).

All cells were grown in Eagle culture medium modified by Dulbecco, and supplemented by 10% fetal calf serum and kept in incubator at 37° C. in a humidified atmosphere.

Cytotoxicity Assay

Cell lysis induced by the recombinant protein sp24-MnSOD was measured through the release of the enzyme lactate dehydrogenase (LDH). The protein was added to the cells MCF-7, A-2780, HUH-7, DU-145, A375 in exponential growth at a concentration ranging from 0.06 and 1 µM. The release of LDH in the supernatant culture medium was quantified at different times (24 h), using the Cytotox 96 non-radioactive cytotoxicity assay kit from Promega, according to the instructions provided by Promega. The experiments were performed in triplicate, using different preparations.

Results

TABLE I

Cytotoxic effect of sp24-MnSOD
(rMnSOD long form) on human cancer cells

| Cells | LDH release (SP24-MnSOD-Synthetic) | LDH release W.Type SOD. (SIGMA) |
|---|---|---|
| MCF-7 Ca breast | 90% | 7% |
| A2780 Ovarian Ca | 95% | 3% |
| HUH-7 HCC | 77% | 4% |
| A375 Melanoma | 78% | 5% |
| DU145 Prostate Ca | 76% | 4% |

After 24 hours of incubation of sp24-MnSOD at a concentration of 1.5 µM, the release of the enzyme lactate dehydrogenase from the cells indicates a cytotoxicity and therefore a mortality that varies, depending on the cells. What is very noticeable is that the wild-type protein exerts a cytotoxic activity very weak compared to that of the protein sp24-MnSOD.

The same effect was observed with sp6-MnSOD (rMnSOD short form).

EXAMPLE 3: ASSESSMENT OF MANGANESE PRESENT IN SP24-MNSOD-SYNTHETIC (OR RMNSOD LONG FORM) COMPARED TO THE AMOUNT EXPRESSED BY THE WILD-TYPE MNSOD, BY ATOMIC ABSORPTION SPECTROPHOTOMETRY

Materials and Methods

The Manganese Superoxide (hMnSOD) is a mitochondrial metal enzyme and consists of 4 identical monomer units composed of 22 kDa. Each monomer contains, at the center of the molecule, a Manganese (II)/(III) ion which is surrounded by a trigonal pyramid linked to three histidine residues, an aspartate residue and a solvent molecule (Jan-Ling Hsu, et al., 1996, Karuppiah Chockalingam, et al. 2006).

Manganese is commonly quantified by an examination of atomic absorption spectrometry. The measurement is performed using a graphite furnace equipped with a correction of background with Zeeman effect. A pyrolytic pipe coated with graphite THGA (Perkin-Elmer) placed on an integrated platform, 'Lvov-type', was used to quantify the metal. A normal solution of Mg in 2.5% $HNO_3$ (Spectrascan) was used as a mother solution for the construction of the calibration curve at 3 points. Each measurement was carried out in triplicate. A modifying matrix was added (0.015 mg Pd and 0.01 mg Mg $(NO_3)_2$. The protein concentration of SOD samples, prior to the quantitative analysis of Mn was assessed using the Protein Assay Bio-Rad (Lowry).

Results

Assessment of the amount of manganese contained in rMnSOD long form is reported in Table II.

TABLE II quantitive examination of manganese present
in the molecule sp-24-MnSOD Manganese present in sp24-MnSOD-Synthetic
0.01 atoms/monomer
Manganese present in the MnSOD w.type (SIGMA)
0.6-0.7 atoms/monomer The atomic absorption analysis of rMnSOD long form has shown that in each monomer there is a number of manganese atoms equal to 0.014. These data suggest that the manganese is not the primary metal in rMnSOD. The examination of the MnSOD wild-type has shown, however, the presence of 0.6-0.7 manganese atoms for each monomer.

A similar result was observed with sp6-MnSOD (rMnSOD short form).

EXAMPLE 4: PROTECTIVE AND RESTORATIVE ACTIVITIES OF SYNTHETIC SP24-MNSOD (RMNSOD LONG FORM) ON THE HUMAN RETINA

Materials and Methods

Oct-microperimetric exam with the instrument (Spectral OCT/SLO Otinophthalmic of America Technologies Inc. Canada) (Spaide R F et al., 2008, Fenolland J R et al. 2011).

Preparation of Eye Drops (Eye Lotion)

The eye drop solution was prepared by dissolving 100 µg of sp24-MnSOD in 100 ml of 0.9% saline solution. 10 mg of benzalkonium chloride were then added to the solution. The pH of the solution was adjusted to 7.00.

Two drops of eye preparation were administered, twice a day, to three patients with Myopic Retinopaty for twelve months.

Results

From the "oct microperimetrical" assay, a spot was observed in the retina. The spot assesses quantitatively the sensitivity of the retina to detect and transmit light stimulus, for each area, ranging from zero (red) to sixteen (green). The latter is an indication of an optimal retinal function. The initial examination carried out on the patient, as indicated above, showed a single green area, while most of the areas were red (FIG. 1). After the use of eye drop preparation containing sp24-MnSOD, administered to the patient for twelve months, every day, the examination of the retinal area showed the presence of five green areas (FIG. 2). This result suggests that the retinal cells of the affected area have doubled and are able to detect and transmit light signal. This results demonstrate that the reparative effectiveness of the rMnSOD long form based eye drops, and the reliability of the assay.

The same effect was observed with sp6-MnSOD (rMnSOD short form).

EXAMPLE 5: INHIBITION OF CATARACTOGENESIS BY THE USE OF EYE-DROPS CONTAINING THE SYNTHETIC P24-MNSOD-AFTER EXPOSURE TO UV RAYS

Oxidative stress caused by exposure to ultraviolet radiation of the eye structures exerts a key role in cataractogenesis. In the present invention, the inventor wanted to assess whether the sp24-MnSOD-synthetic could provide protection to the crystalline lens of rabbit eyes exposed to high doses of ultraviolet radiations (UV) emitted by a quartz lamp jeloprotect—double irradiation 220 v-w 30-2540 amperes (McCourt E A, et al. 2010, Fujiwara T, et al. 2009).

Material and Methods

Normal NZW rabbits (Charles River code 052) were exposed to ultraviolet radiation in the presence or absence of a collyrium of 10 ml, containing 100 µg of sp24-MnSOD-synthetic dissolved in 0.9% NaCl+10 mg of benzalkonium chloride, administering 2 drops/eye/day for 15 days. At the end of the experiments, the rabbits were sacrificed and the eyes analyzed histologically to study structural modifications. Similarly, and as negative control, an eye drop containing the comparative wild type MnSOD was used at the same concentration and the same composition.

Results

The treatment of the eyes exposed to UV with the drops containing the synthetic sp24-MnSOD- has shown that the protein exerts a significant protective role on the crystalline lens of rabbits. Protection is evidenced by the maintenance of the integrity of the crystalline lens which showed a normal transparency (FIG. 3A). This result suggests that the synthetic-sp24-MnSOD reduces oxidative stress caused by UV radiations (lamp 220-v-w-2540 30 Ampere), preventing them from damaging the ocular structures and in particular the crystalline. The treatment of rabbit eyes with a similar eye drops containing the comparative MnSOD w.type gave completely negative results shows that, in this case, the lenses were completely destroyed (FIG. 3B). In conclusion, the administration of eye drops containing the synthetic sp24-MnSOD, in rabbit eyes exposed to ultraviolet radiation, provides significant protection against the process of cataractogenesis.

The same effect was observed with sp6-MnSOD (rMnSOD short form).

Therefore, the proteins of the invention may be used for the prevention and/or treatment of cataracts.

EXAMPLE 6: EFFECT OF THE PROTEINS OF THE INVENTION ON LEUKEMIA CELLS

Materials and Methods
Culture Cells

Lymphoblastic leukemia cells were collected from one patient diagnosed and treated for T-cell acute lymphoblastic leukemia (T-ALL) at the Pediatric Oncology Unit of Second University of Naples and purified by bone marrow using Ficoll Hystopaque density gradient centrifugation. Clinical characteristics of patient at diagnosis were: age 3 years old, white blood count 197000/µL, FAB classification L2, good prednisone responder and early T immunophenotype.

Leukemic lymphoblasts, Jurkat cells and lymphocytes from healthy donors (as control) were cultured at a density of $1 \times 10^6$ cells/mL in RPMI media supplemented with 1% Penstrep and 10% FBS in a humidified atmosphere containing 5% $CO_2$ at 37° C.

Cell Viability Assay

Cell viability was analyzed by MTT [3-(4, 5-dimethyl-thiazol-2-yl)-2, 5-diphenyl tetrazolium bromide] assay. Cells were seeded in 96-well plates at the density of $1 \times 10^3$ cells/well in a final volume of 100 µL. Cells were then incubated at 37° C. in a humidified atmosphere to allow exponential growth. After 72 hours of growth, cells were treated with rMnSOD long form at a final concentration ranging from 0.0067 µM to 0.67 µM, for 5 hours. At 5 hours from the treatment, cells were exposed to 10% MTT for 3 hours at 37° C. to form formazan crystals by reacting with metabolically active cells. The formazan crystals were solubilized in a 1N isopropanol/HCL 10% solution at 37° C. for 30 minutes. The absorbance at 595 nm was then determined. Cell viability was determined by the formula: Cell viability (%)=(absorbance of the treated wells−absorbance of the blank control wells)/(absorbance of the negative control wells−absorbance of the blank control wells)×100%. Control cells (leukemic lymphoblasts, Jurkat cells and lymphocytes) were cultured under identical conditions but in the absence of rMnSOD long or short form. All experiments were performed in triplicate.

Cell Cycle Analysis

Jurkat cells were seeded at density of $1 \times 10^6$ and then incubated 24 hours in humidified atmosphere at 37° C. The next day, the cells were treated with 0.067 µM rMnSOD long form for 5 hours in humidified atmosphere at 37° C. After incubation, cells were washed in PBS 1×, pelleted, and stained with Propidium Iodide (PI) solution (50 mg PI in 0.1% Sodium citrate, 0.1% NP40, pH 7.4) for 30 minutes at 4° C. in the dark. Flow cytometry analysis was performed using a FACScan flow cytometer (Becton Dickinson, San Jose, Calif.). To evaluate cell cycle, PI fluorescence was collected as FL2 (linear scale) by the ModFIT software (Becton Dickinson). The intracellular DNA content evaluation, was performed by analyzing 20000 events for each point in triplicate. Each experiment gave a S.D. less than 5%.

Evaluation of Apoptosis by DNA-Flow Cytometry

Apoptotic cell death was analyzed by Annexin-V-FITC staining Annexin-V-FITC binds to phosphatidylserine residues, which are translocated from the inner to the outer leaflet of the plasma membrane during the early stages of apoptosis. Apoptotic cell labeling was performed using an Annexin-V kit (MedSystems Diagnostics, Wien, Austria). Jurkat cells were seeded at the density $1 \times 10^6$ and then incubated 24 hours in humidified atmosphere at 37° C. Then the cells were treated with 0.067 µM rMnSOD long form and incubated at 37° C. for 5 hours. After the incubation the cells were collected and centrifuged for 5 minutes at 1,500 rpm. Pellet was washed in PBS 1×, incubated with Annexin-V-FITC in a binding buffer (10 mM HEPES, pH 7.4, 150 mM NaCl, 5 mM KCl, 1 mM $MgCl_2$, 2.5 mM $CaCl_2$) for 30 minutes at 4° C. Analysis of apoptotic cells was performed by flow cytometry (FACScan, Becton Dickinson). $10 \times 10^4$ events were acquired for each sample. Analysis were carried out in triplicate.

Immunocytochemistry at Light Microscopy

Lymphoblastic leukemia cells, Jurkat cells, and lymphocytes were incubated for five hours in the presence or absence of rMnSOD long form at a final concentrations ranging from 0.0067 to 0.67 µM. Subsequently, a cytospin was used to smear cells onto slides. The smears were fixed in Zamboni solution (4% paraformaldehyde, 15% picric acid) for 60 minutes and then washed with 1×PBS and incubated for five minutes with 3% hydrogen peroxide to quench endogenous peroxidase activity. Immunostaining was performed using the DAKO LSA+System HRP kit. Rabbit anti-rMnSOD-Lp (1:200), was incubated on slides for 30 minutes, followed by incubation with the biotinylated secondary antibody for 30 minutes and peroxidase-labeled streptavidin for 30 minutes. To complete the reaction, a substrate-chromogen solution was used. The smears were counterstained with hematoxylin.

Determination of the Apoptotic Index

Apoptotic cells and bodies were counted from several areas of each sample. The apoptotic index (AI) was estimated as the number of apoptotic cells and/or bodies per 1000 tumor cells, expressed in percentages.

Immunogold Method at Transmission Electron Microscopy

Both leukemic cells and lymphocytes were incubated for six hours in the presence or absence of rMnSOD long form at a final concentration ranging from 0.0067 to 0.67 µM. The cells were then fixed using 0.1% glutaraldehyde and 4% paraformaldehyde in 0.1 M sodium cacodylate buffer for 60 minutes at room temperature and washed twice in 0.1 M sodium cacodylate buffer. Samples were then treated with 1% OsO4 for 10 minutes, dehydrated, embedded in Epon 812, and polymerized at 60° C. for 24 hours. Ultrathin sections were prepared using a Leica Ultracut UCT ultramicrotome and mounted on nickel grids. The sections were subsequently subjected to antigen unmasking in citrate buffer, incubated with 10% hydrogen peroxide for 10 minutes, washed 3 times in PBS 0.9% for 5 minutes, and incubated in BSA 1% and glycine 0.15% in PBS for 30 minutes. The samples were incubated with polyclonal rabbit anti-rMnSOD-Lp (1:20) in Tris-HCl 0.05 mol/L with 1% BSA overnight at 4° C., washed three times in PBS 0.9% for 10 minutes, and incubated with a donkey anti-rabbit secondary antibody conjugated to 15 nm colloidal gold diluted (1:10) in 0.1% BSA for 2 hours at room temperature. The sections were washed in PBS (pH 7.4) and distilled water prior to counterstaining with uranyl acetate and lead citrate. Ultrathin sections were examined using a LEO 912AB Zeiss transmission electron microscope.

Protein Extraction and Western Blot Analysis.

Protein extraction was performed on ice for 30 minutes using lysis-buffer (1M Tris-HCl pH 8, 5M NaCl, 0.5 M NaF, 100% NP40) with protease-inhibitors (4 µL/mL PMSF, 2 µL/mL aprotinin and pepstatin, 1 µL/mL Na Ortovanadate). Cell lysates were centrifuged at 20,000 g for 2 minutes at 4° C., and proteins were extracted from supernatant. Total protein concentration was determined using Bradford assay (Bio-Rad). For Western blot analysis, 30 µg of total protein was run on 10% polyacrylammide gel and blotted onto PVDF membrane (Millipore, Marlborough, Mass.). The membrane was blocked in 5% nonfat dry milk dissolved in TBS buffer (2 mM Tris, 13.7 mM NaCl, 0.1% tween-20, pH 7.6) overnight. All washes were performed in TBS buffer. Immunoblotting was performed using primary antibodies against Bcl-2 (100), Bax (N20), AKT (H-136), pAKT (Ser473), ERK (G-12), and pERK (E-4) (Santacruz Biotechnology, INC) (1:500) incubated for 1 hour. Secondary antibodies (Santacruz Biotechnology 1:5000) were incubated at room temperature for 1 hour. Bands were visualized using a chemiluminescent system (ECL-Amersham). The intensity of each band was acquired with a CCD camera and analyzed with Quantity One 1-D analysis software (Biorad Laboratories). Results were normalized against the level of α-actin expression in each sample.

Detection of Reactive Oxygen Species

Cell samples were pretreated with or without 10 mM NAC (Sigma-Aldrich, Saint Louis, USA) at 37° C. for 20 minutes, and incubated with 0.067 µM rMnSOD long form for 5 hours, then the cells were washed with PBS 1× and incubated with 10 µM 2',7'-dichlorodihydrofluorescein diacetate (DCFH-DA-Cayman, Baverno, Italy) at 37° C. for 20 minutes. DCFH-DA diffused into cells is deacetylated by cellular esterases to non-fluorescent 2',7'-Dichlorodihydrofluorescin (DCFH), which is rapidly oxidized to highly fluorescent 2',7'-Dichlorodihydrofluorescein (DCF) by ROS. The fluorescence intensity is proportional to ROS levels within the cell cytosol; the fluorescence intensity was assessed using a Hitachi (Model U-2000) double-beam spectrofluorimeter with excitation at 484 nm and emission at 530 nm. Background fluorescence (conversion of DCFH-DA in absence of homogenate) was corrected by the inclusion of parallel blanks.

Results

Effects of rMnSOD Long Form on Growth Inhibition on Human T-ALL Cells, Jurkat Cells and Lymphocytes.

Cells were cultured and monitored for 3 days to assess cellular concentration and proliferation using Trypan blue exclusion assay and MTT tests (Table III).

TABLE III

| | 3 day-culture cell viability | | |
|---|---|---|---|
| | Cell Concentration | Trypan Blue | Morphology |
| | A | | |
| T-leukemic cells | | | |
| T0 | 1000000/mL | 78% | NM. ND. Clump absent |
| T1 | 400000/mL | 87% | NM. ND. Clump absent |
| T2 | 400000/mL | 65% | NM. ID. Clump present |
| | B | | |
| Jurkat cells | 800000/mL | 100% | NM. ID. Clump present |
| | C | | |
| Normal Lymphocytes | | | |
| T0 | 1200000/mL | 100% | NM. ND. Clump absent |
| T1 | 800000/mL | 90% | NM. ID. Clump absent |
| T2 | 800000/mL | 70% | NM. ID. Clump present |

NM: normal morphology;
ND: normal density;
ID: increased density

To perform the experiments with the optimal dose of rMnSOD long form, the inventor initially determined the dose-dependent survival rate of Jurkat and T-ALL upon rMnSOD long form treatment. The inventor observed, based on Trypan blue exclusion assay and MTT tests, a less than 5% cell death after 5 hours treatment with 0.003 µM rMnSOD long form, whereas a significant reduction in cell viability (by ~30%, data not shown) was induced by a 5 hours treatment with 0.067 µM rMnSOD long form. Thus, 0.067 µM rMnSOD long form was selected for the subsequent experiments to minimize the apoptosis-induced alteration in protein expression.

In details, after 72 hours of growth, cells were treated with 0.067 µM rMnSOD long form for 5 hours in culture. The inventor observed, with MTT test, a proliferation rate of 1% T-ALL cells, 40% Jurkat and 70% lymphocytes (FIG. 4A).

Moreover with Trypan blue exclusion assay, performed in the same conditions, the inventor observed a growth inhibition of 99% T-ALL cells, 60% Jurkat and 30% lymphocytes (FIG. 4B). Spontaneous proliferation curves of Jurkat cells line, T-ALL and lymphocytes were used as normalized controls. These curves showed an increase of Jurkat cell's growth, a decrease of lymphocyte growth after 48 h and a slight decrease followed by a stabilization of T-cell ALL's growth after 48 h to 96 h (FIG. 4C).

The same effect was observed with rMnSOD short form.

Effect of rMnSOD Long Form on Apoptosis Induction

After the treatment with 0.067 µM rMnSOD, the inventor evaluated the induction of apoptosis on Jurkat cells by FACS analysis, after staining with Annexin-V-FITC and PI, as above described. As shown in FIG. 5 and Table IV, a significant increase of apoptotic cells compared to control cells has been detected. In details, the inventor found that the treatments with 0.067 µM rMnSOD long form for 5 hours induced apoptosis in 23.7% of Jurkat cells, compared to 5% untreated cells.

TABLE IV

Cell Cycle analysis

| | UL Necrosis | UR Late Apoptosis | LL Living Cells | LR Early Apoptosis |
|---|---|---|---|---|
| CTR | 3.8 | 5 | 90.8 | 0.4 |
| rMnSOD 0.067 µM | 2.5 | 23.7 | 67.1 | 6.6 |

Insets, % of positive cells.
UL = Upper Left (necrosis);
UR = Upper Right (late apoptosis);
LL = Lower Left (viable);
LR = Lower Right (early apoptosis).
Untreated cells, CTR.

FIG. 5 (B) shows cell cycle FACS analysis after Propidium Iodide (PI) incorporation in Jurkat cells. The inventor observed that 0.067 µM rMnSOD long form did not induce significant changes in cell cycle distribution if compared to untreated cells.

The same effect was observed with rMnSOD short form.

Light Microscopy

The treatments performed respectively with 0.0067, 0.067 and 0.67 µM rMnSOD long form for 5 hours on the three cell populations gave the following percentages of labeled cells: 40%, 60% and 76% of cultured leukemic T cells; 60%, 73% and 100% of Jurkat cells and 60%, 70% and 75% of lymphocytes, while the controls displayed no labeling (FIG. 6A). Overall, these results indicate that most cells internalized rMnSOD, as they displayed both mainly cytoplasmic and less nuclear immunoreactivity (FIG. 7A-F; H-J). The percentages of viability as a result of the three concentrations of rMnSOD long form tested are reported in FIG. 6B.

The same effect was observed with rMnSOD short form.

Leukemic T-Cell and Jurkat Cells

The T leukemic cells and Jurkat cells, treated with 0.67 µM rMnSOD long form, displayed cytoplasmic and nuclear positivity as well as rupture of the plasma membrane, (FIGS. 7F; 9E-F). In contrast, both the cells treated with 0.0067 and 0.067 µM rMnSOD long form showed cytoplasmic positivity as well as the pre-apoptotic changes of early and complete nuclear and cytoplasmic fragmentation (FIGS. 7A-E; 9A-D).

The same effect was observed with rMnSOD short form.

Lymphocytes

Lymphocytes treated with 0.67 µM rMnSOD long form showed cytoplasmic and slight nuclear positivity as well as rupture of the plasma membrane. (FIGS. 7J; 9K-L); whereas cells treated with 0.0067 or 0.067 µM rMnSOD long form showed no morphological alterations (FIGS. 7H-J; 9I-L). Lymphocytes (not treated with rMnSOD) displayed no positivity (FIGS. 7G; 9G-H). Together, these findings indicate that 0.0067 and 0.067 µM rMnSOD long form cause apoptosis of only leukemic cells, instead 0.67 µM rMnSOD long form is a toxic concentration.

The same effect was observed with rMnSOD short form.

Determination of the Apoptotic Index

The number of the cells displaying both apoptotic nuclear and cytoplasmic fragmentation, is reported in FIG. 8. Apoptotic cells and bodies were counted from several areas of each sample. The apoptotic index (AI) was estimated as the number of apoptotic cells and/or bodies per 1000 tumor cells, expressed in percentages. rMnSOD long form treatment induces apoptosis in both cultured ALL patient cells and in Jurkat cell line, without adverse effects on lymphocytes. In fact it is shown that 0.067 µM rMnSOD long form causes apoptosis of leukemic T cells and of Jurkat cells in vitro and it is observed (by MTT assay) a survival rate of 1% T-ALL cells, 40% Jurkat and 70% lymphocytes after treatment with rMnSOD long form.

The same effect was observed with rMnSOD short form.

Transmission Electron Microscopy

The inventor used transmission electron microscopy (TEM) to confirm the internalization of rMnSOD long form by leukemic T cells, Jurkat cells, and lymphocytes treated with 0.0067, 0.067 and 0.67 µM of rMnSOD. The TEM results show colloidal gold particles (10 nm) dispersed mainly in the cytoplasm and sometimes near the mitochondrial envelope (FIGS. 9A-F; I-L), confirming that rMnSOD long form enters the cells. The internalization of rMnSOD long form was also evident in nuclear and cytoplasmic apoptotic fragments (FIGS. 9C-D) and in damaged cells (FIGS. 9E-F). rMnSOD long form also enters lymphocytes, as indicated by the presence of the 10 nm-gold particles distributed in the cytoplasm (FIGS. 9I-L) after the 5 hour treatment. No labeling was observed in untreated cells (FIGS. 9G-H).

The same effect was observed with rMnSOD short form.

rMnSOD Long Form Treatment on Survival Pathway

To determine the mechanism of growth inhibition by rMnSOD long form in more details, the inventor analyzed the apoptotic profile after treatment with rMnSOD. In particular the inventor evaluate expression of Bcl-2 and Bax in leukemic T cells, Jurkat cells, and lymphocytes at a final concentration ranging from 0.0067 to 0.67 µM of rMnSOD.

The treatment of leukemic T cells with 0.067 µM rMnSOD long form induces the expression of pro-apoptotic Bax and suppresses expression of Bcl-2 in comparison to non-treated cells (FIG. 10A-D). Jurkat cells treated with 0.067 µM rMnSOD long form also showed increased expression of Bax and decreased expression of Bcl-2 (FIG. 10B-E). Conversely, the treatment of lymphocytes with 0.067 µM rMnSOD long form did not affect Bcl-2 or Bax expression in comparison to non-treated counterparts (FIG. 10C-F).

The same effect was observed with rMnSOD short form.
rMnSOD Long Form Treatment on Proliferation Pathway To analyze if rMnSOD long form acts also on key regulators of proliferation pathways, the inventor assess AKT and ERK phosphorylation respect to basal levels. The inventor founded that rMnSOD long form treatment did not affect AKT phosphorylation in all tested samples. No changes in the expression of phosphorylated ERK, following rMnSOD long form treatment, resulted in T-ALL cells and in lymphocytes (FIG. 10A, C), while a slightly decreased expression of phosphorylated ERK was detected in Jurkat cells (FIG. 10B), thus indicating that growth inhibition after rMnSOD long form treatment could be not influenced by MAP/ERK chinase pathway but by apoptotic pathway, except for Jurkat cells that are a model with altered multiple pathways.

The same effect was observed with rMnSOD short form.
Detection of Reactive Oxygen Species N-acetylcysteine (NAC) resulted in blocking of rMn-SOD-induced ROS generation, as shown in FIG. 11. In fact 10 mM NAC induced a DCF decrease, following incubation with 0.067 μM rMnSOD, while the treatment without NAC, showed fluorescence comparable to the control. These data suggest that 0.067 μM rMnSOD long form induces ROS production in much higher amounts than in controls, as expected.

The same effect was observed with rMnSOD short form.

It is well known that leukemic cells produce high levels of reactive oxygen species and have a disturbance of the protective role of enzyme against free radical. This variability of cell antioxidant machinery and ROS production, according to the cancer type, may be explained by the level of antioxidant defense which lead to a ROS production effective in generating neoplastic cell transformation but not enough to trigger apoptosis. Increasing evidence demonstrates the key role of ROS in the regulation of cell life and death. The toxic potential of ROS is able to activate the immune response.

Thus, the development of new therapeutic interventions must deal with the duality of ROS in both protective cytotoxic against "non self" action and injurious action of their exceeding accumulation able to induce carcinogenesis (Manda et al., 2009). Similarly the rMnSOD long form shows a duality of action too, being able to trigger apoptotic death of cancer cells while oxygenates the healthy cells, or, if it exceeds the ability of catalase to transform the peroxide into oxygen and water, can induce necrosis in both tumor cells and healthy cells (Mancini et al., 2006). So the redox balance appears to be the main mechanism of carcinogenesis control (Manda et al., 2009; Barbosa et al., 2012). In this study, the inventor demonstrated that rMnSOD long form treatment induce apoptosis in both cultured ALL patient cells and in Jurkat cell line, without adverse effects on lymphocytes. In fact the inventor showed that 0.067 μM rMnSOD long form causes apoptosis of leukemic T cells and of Jurkat cells in vitro and the inventor observed (by MTT assay) a survival rate of 1% T-ALL cells, 40% Jurkat and 70% lymphocytes after treatment with rMnSOD. Moreover, the inventor showed that 0.067 μM rMnSOD long form upregulates the pro-apoptotic protein Bax and inhibits the anti-apoptotic protein Bcl-2 in leukemic T cells. This data are in accordance with Mancini et al. (Mancini et al., 2006) on breast cancer cells who confirm a strong upregulation of pro-apoptotic Bax gene expression in the presence of rMn-SOD, suggesting that this treatment might induce the apoptotic cascade. The possible involvement of an apoptotic mechanism was suggested by the strong inhibition of anti-apoptotic Bcl-2 gene expression detected in tumor cells in the presence of rMnSOD (Mancini et al., 2008). In addition, FACS analysis of cells treated with 0.067 μM rMnSOD long form displayed an evident increase of apoptotic cells in 23.7% of Jurkat cells, as compared to control cells.

Interestingly, leukemic cells internalize the exogenous rMnSOD long form that converts free radicals present in $H_2O_2$. Notably, catalase detoxifies $H_2O_2$ into molecular oxygen and it is usually in lower amount in leukemic cells than in healthy cells. (Battisti et al., 2008). Thus, treatment with rMnSOD long form may lead to accumulation of $H_2O_2$ and subsequent death of leukemic cells. In contrast, lymphocytes do not show this reduction in catalase activity and can tolerate high levels of endogenous $H_2O_2$ production. However, a concentration of 0.67 μM rMnSOD long form is toxic to leukemic cells and to lymphocytes; in fact at this concentration the rMnSOD long form induces necrosis due to a stechiometric imbalance that is created between the enzymes MnSOD and catalase. The same effect was observed with rMnSOD short form.

In conclusion, the present findings suggest that rMnSOD long and short forms could be considered as an associated additional treatment for leukemia, particularly as low concentrations of rMnSOD long or short form seem specifically toxic to cancer cells while having a protective effect on healthy cells. According to the current knowledge about the therapeutic target role of the redox balance (Barbosa et al., 2012; Manda et al., 2009), these results suggest an action for the rMnSOD long and short forms which would achieve a good therapeutic efficiency and no side effects.

EXAMPLE 7: EFFECT OF RMNSOD LONG FORM ON NEUROBLASTOMA

The effect of the novel isoforms of recombinant human manganese superoxide dismutase (rMnSOD) with long and short leader peptide were investigated in an in vitro model of cell culture (neuroblastome SK-N-BE cells cell cultures). Several lines of evidence suggested indicated that the new molecule acts as an anticancer agent.

To evaluate this hypothesis, the inventor treated our neuron-like cell cultures with two different rMnSOD long form with long and short leader sequence.

Cells growing in their specific medium were incubated in the presence of rMnSOD (long and short rMnSOD) added to the culture medium. To determine the cytotoxicity of both proteins, cells were examined to light microscope for induction of cytopathic changes as exemplified in the FIG. 12 (a-b-c) with the long form.

Both the recombinant proteins were rapidly internalized by neuron-like cells and show tumorigenic activity on cells, with sign of toxicity after 5-6 h in culture.
Methods 20000 neuroblastome SK-N-BE cells were seeded in 24-multiwell (FALCON) with MEM medium supplemented by 10% FCS (GIBCO). 24 hr later the long and the short rMnSOD (1.25 μM) was added in each well. After 24 and 48 hr the cells were washed twice with PBS. Then the cytotoxic activity of both proteins rMnSOD were evaluated by using the LDH tests accordingly to method described in (Int. J. of Cancer—123, 2684-2695, 2008).
Results The results show that the cytotoxic effect of rMnSOD long form on neuroblastome SK-N-BE cells generate its killing effect (FIG. 12a-c).

The same effect was observed with the rMnSOD short form.

In conclusion, these data suggest that the two recombinant iso forms (with the short and long leader sequence) MnSOD are cytotoxic for neuroblastoma cells SK-N-BE, suggesting their use in the treatment of neuroblastoma.

EXAMPLE 8: EFFECT OF RMNSOD LONG FORM ON BRAIN INFLAMMATION

The effect of rMnSOD long form was investigated by an in vivo animal model of middle-aged mice. Several lines of evidence suggested that rMnSOD long form is able to strongly blunt oxidative stress and tissue inflammation. These biological processes appear to bear critical components involved in physiological aging and pathological neuro-degeneration, thus suggesting that the activity of the rMnSOD long form could partially modulate both these processes and potentially reduce some of their adverse aspects effects.

To evaluate this hypothesis the inventor treated middle-aged mice Balb-C (18 months of age) with rMnSOD long form by chronic intra-nasal administration. (2 µg of protein in 50 µl/day)

The present findings show that although no behavioural differences were observed in learning and memory tasks, the biochemical analysis of the cerebral cortices of treated mice in comparison to controls showed a significant decreasing pattern of the expression of 5 proteins involved into inflammatory pathways (BLC, CD30L, Fas Ligand, Kc, TNFR2), paralleled by a lower protein expression trend observed for IL-1Beta and I-Tac. (FIG. 14)

The same effect was observed with rMnSOD short form.
Material and Methods
Simultaneous Detection of Cytokine Levels in Mice Cortical Tissues.

Simultaneous detection of multiple mouse cytokines was performed with Mouse Cytokine Antibody Array-Membrane (Abcam, Cambridge, UK) according to manufacturer's instructions. On the membrane were spotted antibodies against 97 mouse cytokines, positive (biotin-conjugated IgG protein) and negative (buffer used to dilute antibodies printed on the array) controls. Briefly the cortical tissues of mice treated with rMnSOD long form and saline solution were lysed with lysis buffer containing protease inhibitors, homogenized and clarified by centrifugation. The membrane was incubated with blocking buffer for 30 min at room temperature (RT), then with 500 µg of total proteins in blocking buffer overnight at 4° C. After 3 washing with wash buffer I and 3 washing with wash buffer II, the membrane was incubated with biotin conjugated anti-cytokines overnight at 4° C. After 3 washing with wash buffer I and 3 washing with wash buffer II, the membrane was incubated with HRP-conjugated streptavidin overnight at 4° C. The chemiluminescent signals were revealed with detection buffer. The membrane was transferred to imaging system and exposed for 2 min. The raw densitometry data were subtracted from the background (negative control probes) and normalized to the positive probe signals for comparison of results across multiple arrays.

In conclusion, these data suggest that the recombinant iso forms of manganese superoxide dismutase of the invention as long or short forms are able to enter inside neuronal cells and modify brain protein expression. This suggests their effects on central nervous system and particularly in neuro-degenerative diseases as possible pharmacological tool to develop innovative therapies.

EXAMPLE 9: COMPARISON BETWEEN THE RMNSOD LONG AND SHORT FORMS OF THE INVENTION AND DIFFERENT RECOMBINANT MNSOD

The cytotoxic effect on tumor cells of the present proteins (Long and Short rMnSOD) were examined in comparison with two others human recombinant SOD2:
the first, SEQ ID No. 7 (called SIGMA), is a human recombinant SOD2, a full-length GST-tagged protein, with the leader peptide of 24 aminoacids and without 5 aminoacids at C-terminal;
the second, SEQ ID No. 8 (called Abcam), is a human recombinant SOD2, a full-length protein, without the leader peptide of 24 aminoacids, without tag and without 5 aminoacids at C-terminal.

```
Sequence of comparative rMnSOD (named SIGMA, SEQ
ID NO.7) :
MSPILGYWKI KGLDQPTRLL LEYLEEKYEE HLYERDEGDK

WRNKKFELGL EFPNLPYYID GDVKLTQSMA IIRYIADKHN

MLGGCPKERA EISMLEGAVL DIRYGVSRIA YSKDFETLKV

DFLSKLPEML KMFEDRLCHK TYLNGDHVTH PDFMLYDALD

VVLYMDPMCL DAFPKLVCFK KRIEAIPQID KYLKSSKYIA

WPLQGWQATF GGGDHPPKSD LVPRGSMLSR AVCGTSRQLA

TVLGYLGSRQ KHSLPDLPYD YGALEPHINA QIMQLHHSKH

HAAIVNNLNV TEEKYQEALA KGDVTAQIAL QPALKFNGGG

HINHPIFWTN LSPNGGGEPK GELLEAIKRD FGSFDKFKEK

LTAASVGVQG PGWGWLGFNK ERGHLQIAAC PNQDPLQGTT

GLIPLLGIDV WEHAYYLQYK NVRPDYLKAI WNVINWENVT

ERYMACKK

Sequence of comparative rMnSOD (named Abcam, SEQ
ID No. 8):
KHSLPDLPYD YGALEPHINA QIMQLHHSKH HAAYVNNLNV

TEEKYQEALA KGDVTAQIAL QPALKFNGGG HINHSIFWTN

LSPNGGGEPK GELLEAIKRD FGSFDKFKEK LTAASVGVQG

SGWGWLGFNK ERGHLQIAAC PNQDPLQGTT GLIPLLGIDV

WEHAYYLQYK NVRPDYLKAI WNVINWENVT ERYMACKK
```

The cytotoxic effect of two comparative recombinant proteins has been assessed through LDH assay (Table V), at the concentration of 1.5 µM, and compared to the effect achieved by the rMnSOD proteins of the present invention (rMnSOD Long Mancini and rMnSOD Short Mancini).

TABLE V

Citotoxic effect of different rMnSOD on various cell lines

|  | MCF-7 | MiaPaCa | OVCAR3 | A375 | MCF-10 |
|---|---|---|---|---|---|
| rMnSOD Long Mancini 1.5 μM | 97% | 86% | 94% | 68% | 13.50% |
| rMnSOD Short Mancini 1.5 μM | 98.10% | 85.80% | 95% | 71% | 12% |
| rMnSOD abcam 1.5 μM | 12.20% | 2.30% | 9.90% | 14% | 11% |
| rMnSOD SIGMA 1.5 μM | 7.30% | 4.15% | 8% | 15.30% | 11.70% |
| cisPt 25 μM | 38.80% | 36.90% | 20.30% | 35% | 51% |
| cisPt 1.5 μM | 15.30% | 5.80% | 2.20% | 12% | 17.70% |
| CRTL (glicerol buf. Acqueous) | 2.20% | 2.20% | 2.20% | 2% | 2% |
| CRTL (HEPES 20 mM) | 6.60% | 6.60% | 6.60% | 6.60% | 6.60% |

The results are also illustrated on FIG. 15. Cell lysis induced upon four different rMnSOD treatments was measured through release of LDH enzyme. rMnSODs were added to exponentially growing cultures to a final concentration of 1.5 μM (unless differently indicated), and the release of LDH into the medium supernatant was measured at indicated times post application, using the CytoTox 96 nonradioactive cytotoxicity assay kit from Promega, according to the manufacturer's recommendations. Experiments were performed in triplicate, using different rMnSOD preparations (rMnSOD long Mancini, rMnSOD long Mancini rMnSOD SIGMA and rMnSOD Abcam) and the LDH release was expressed as the fraction of total LDH released upon detergent treatment.

LDH release into the culture supernatant, expressed as a percentage of the total LDH (from cell lysis induced by detergent treatment). Approximately 3% LDH was found in the medium of untreated cultures. rMnSODs were tested for their cytostatic and cytolytic effects on other human mammary epithelial cell lines of normal (MCF-10) or tumor (MCF-7) origin and on a variety of non-mammary transformed cells (OVCAR-3, Mia PaCa, A-375). rMnSOD (long and short) Mancini induced MCF-7 cell culture to release 97%-98.10% of their LDH content into medium (as compared to the artificial LDH-release induced by detergent treatment), whereas very lower increase in LDH activity could be detected in MCF-10 cell culture supernatants upon application of this recombinant protein versus 12.20% of rMnSOD Abcam and 7.30% of rMnSOD Sigma. The tumor-derived MIA PaCa-2, OVCAR-3, A375 cells all showed a striking sensitivity to rMnSODs Mancini-induced killing.

Then the rMnSOD long and short form of the present invention display improved properties compared to other forms of rMnSOD.

EXAMPLE 10: EFFECT OF THE RECOMBINANT MNSOD OF THE PRESENT INVENTION ON LIVER CIRRHOSIS AND ORGANS FOR GRAFT

High oxidative stress plays a major role in increasing hepatic vascular resistance in cirrhosis, by facilitating liver fibrosis and by increasing hepatic vascular tone. Inventor's study aimed at investigating whether the use of rMnSOD could be a new therapeutic strategy to reduce oxidative stress and portal hypertension in cirrhotic rats. In $CCl_4$ and BDL-cirrhotic rats treated with rMnSOD long form (i.p. 15 μg/Kg/day) or its vehicle for 7 days, mean arterial pressure (MAP), portal pressure (PP) and portal blood flow (PBF) or small mesenteric arterial flow (SMABF) were measures. In addition, in $CCl_4$-cirrhotic rats, we evaluated the hepatic vasodilatatory response to acetylcholine, liver fibrosis with Sirius red staining and hepatic stellate cell activation by α-smooth muscle actin (α-SMA) protein expression. rMnSOD long form treatment significantly reduced PP either in $CCl_4^-$ or BDL-cirrhotic rats without significant changes in splanchnic blood flow, suggesting a reduction in hepatic vascular resistance. MAP was not modified. Reduction in PP was associated with a significant reduction in liver fibrosis, and α-SMA protein expression as well as with improved vasodilatatory response to acetylcholine.

Chronic rMnSOD long form administration to cirrhotic rats reduces portal pressure by reducing hepathic vascular resistance without deleterious effects on systemic hemodynamic, suggesting that it might constitute a new antioxidant to be considered as additional therapy for treating portal hypertension in cirrhosis.

Hepatic microcirculatory dysfunction due to cold storage and warm reperfusion (CS+WR) injury during liver transplantation is partly mediated by oxidative stress and may lead to early graft dysfunction. This is especially relevant when steatotic donors are considered. The inventor aimed at characterizing the effects of rMnSOD on the microcirculation, parenchymal injury and endothelial function of livers undergoing CS+WR.

Oxidative stress and nitric oxide were determined in primary cultured liver endothelial cells cold stored with rMnSOD long form or its vehicle and then warm reperfused. Control and steatotic rats received a single dose of rMnSOD long form or its vehicle 30 min before liver procurement and grafts were cold stored for 0 h (control group) or 16 h. After 1 h of warm reperfusion, hepatic microcirculation, endothelial function and phenotype, and liver injury were analyzed. The antioxidant effects of adding rMnSOD long form to a cold storage solution were also assessed in rat and human livers undergoing CS+WR.

After CS+WR, the liver endothelium exhibited elevated superoxide and diminished nitric oxide levels; these detrimental effects were prevented by rMnSOD. CS+WR control and steatotic rat livers exhibited markedly deteriorated microcirculation and acute endothelial dysfunction development, together with liver damage, inflammation, oxidative stress, and low nitric oxide. rMnSOD long form markedly blunted oxidative stress, which was associated with global improvement in liver damage and microcirculatory derangements. rMnSOD long form addition to cold storage solution maintained its antioxidant capability protecting both rat and human liver tissues.

The same effects were observed with rMnSOD short form.

rMnSOD longand short form represent a new and highly effective therapy to significantly upgrade liver procurement for transplantation.

EXAMPLE 11: EFFECT OF THE RECOMBINANT MNSOD OF THE PRESENT INVENTION ON ROS, IN PARTICULAR IN A MODEL OF DILATED CARDIOMYOPATHY (CMD)

Material and Methods
ROS Measurement Assay

To measure the level of ROS in the kidney, the inventor performed a 2'7' dichloroflurescin diacetate assay as described in (Borrelli, et al., 2011). At the end of the in vivo treatment, rats were anaesthetized and then sacrificed by exsanguinations and the right kidney was quickly stored at −80° C. Later, the kidneys were thawed on ice and weighed. Kidneys were homogenized in 5 mL of Tris-Hcl 40 mM (pH 7.4) with Ultraturrax. Protein concentration was assessed by the Bio-Rad protein assay. 2'7' dichloroflurescin diacetate 5 µM (Molecular Probes) was utilized for the assay from a 500 µM stock. The tissue samples were diluted in a range from 10 000 to 2500 times. The spectrum was analysed from 480 to 525 nm at different times (T0, T10, T30) using a spectrophotometer Jasco FP-777. The levels of ROS were expressed as intensity fluorescence (IF) normalized for grams of tissue and micrograms of proteins.

Results

TABLE VI

ROS quantification in different groups under study

| Sample serum | IF/mg protein | nM DCF/mg protein |
|---|---|---|
| A1 control | 13700 | 590 |
| A2 control + rMnSOD long form | 6263 | 270 |
| B1 CMD | 6312 | 270 |
| B2 CMD + rMnSOD long form | 2854 | 120 |
| C1 CMD | 9928 | 430 |
| C2 CMD + rMnSOD long form | 7001 | 300 |

A1: human normal serum;
A2: human normal serum treated in the presence of rMnSOD long form;
B1: human serum of a patient affected by CDM in the absence of rMnSOD long form;
B2: human serum of a patient affected by CDM in the presence of rMnSOD long form;
DCF: 2'7' dichloroflurescin diacetate;
CDM: Dilated Cardio myopathy;
IF: intensity fluorescence Results from these experiments demonstrated that after only 5 mm incubation with 2 µg of rMnSOD long form and 1 ml of serum derived from patient bearing CMD, the amount of ROS has been strongly reduced, suggesting that a continuously infusion i.v. of rMnSOD long form could reduce the CMD in the patients The same effects were observed with rMnSOD short form.

Then rMnSOD long and short forms are useful for the treatment of CMD.

EXAMPLE 12: PROTECTIVE EFFECT OF THE RECOMBINANT MNSOD OF THE PRESENT INVENTION IN MICE EXPOSED TO THE PROTON RADIATIONS

Material and Methods

Using the model of sublethal whole-body irradiation with protons available at Phasotron of the Joint Institute for Nuclear Research (Dubna), we reconstructed the bone-marrow form of the acute radiation syndrome in mice to test the radioprotective effect of rMnSOD. Male (CBAxC57B16) F1 SPF mice with the average weight of 24 g were exposed to 171 MeV proton beam at the dose of 4 Gy and then subcutaneously treated with either rMnSOD or sodium chloride physiological solution.

Results

After irradiation, the sixfold daily subcutaneous treatment with rMnSOD (long), has provided a statistically significant acceleration of the recovery of thymus and spleen mass and of the number of leukocytes in mice peripheral blood. In contrast, mice irradiated and treated with physiological solution did not demonstrate these positive effects at seventh day after exposure. The number of nucleated cells in bone marrow of irradiated mice has even exceeded its basal level in the control group seven days after irradiation. The rMnSOD-treated group has thus demonstrated a significant hyper restoration of their normal characteristic.

TABLE VII

Treatment of animals in the presence of rMnSOD (long)

| Time after irradiation | Group | Body mass, g | Spleen mass, mg | Thymus mass, mg | BMC, N × 106/femur | Number of leukocytes in PB, N × 109/L | Mitotic index in bone marrow cells, % | Number of aberrant mitoses in bone marrow cells, % |
|---|---|---|---|---|---|---|---|---|
| 43 h | Control | 26.4 ± 1.5 | 126.8 ± 30.5 | 21.4 ± 9.0 | 49.4 ± 5.6 | 9.3 + 2.0 | 2.5 ± 0.9 | 2.2 ± 3.2 |
| | One-time treated with rMnSOD immediately after irradiation | 24.8 ± 1.3 | 29.0 ± 5.1 | 11.8 ± 1.3 | 22.9 ± 2.4 | 0.9 ± 0.3 | 1.3 ± 0.1 | 47.6 ± 2.8 |
| | One-time treated with SCPS immediately after irradiation | 24.2 ± 1.5 | 31.8 ± 1.9 | 11.5 ± 1.0 | 24.2 ± 1.7 | 0.9 ± 0.3 | 1.3 ± 0.2 | 45.9 ± 8.1 |
| Day 7 | One-time treated with rMnSOD immediately after irradiation | 24.6 ± 1.1 | 34.8 ± 3.1 | 14.8 ± 3.4 | 63.1 ± 1.0 | 4.5 ± 0.4 | 1.6 ± 0.3 | 26.7 ± 3.3 |
| | One-time treated with SCPS immediately after irradiation | 24.8 ± 0.8 | 33.2 ± 9.5 | 11.7 ± 1.5 | 64.7 ± 4.9 | 6.1 ± 1.9 | 1.5 ± 0.2 | 22.7 ± 2.9 |
| | Sixfold daily treated with rMnSOD | 25.2 ± 1.9 | 62.2 ± 16.2 | 39.0 ± 18.1 | 79.5 ± 1.7 | 7.4 ± 0.4 | 1.5 ± 0.3 | 29.5 ± 4.8 |
| | Sixfold daily treated with SCPS | 24.6 ± 1.3 | 32.4 ± 3.4 | 13.0 ± 6.2 | 67.9 ± 2.6 | 5.3 ± 1.2 | 1.3 ± 0.2 | 29.4 ± 10.5 |

Irradiation, of different animal groups subcutaneously treated either with rMnSOD solution (1 µg per 0.5 mL) or sodium chloride physiological solution (SCPS) in the volume of 0.5 mL. Three groups of irradiated animals received rMnSOD. Two of them were treated only once immediately after irradiation and were tested after 43 h and 7 days respectively. The third group received sixfold daily treatments with rMnSOD starting with a first injection right after irradiation and was tested at seventh day after exposure. Three other irradiated groups which received SCPS were treated and tested at the same periods of time as the rMnSOD ones. The control unirradiated group did not receive any treatment.

The results on the state of organs of the immune system and hemopoiesis indicate the therapeutic effect of rMnSOD in treating the acute radiation disease induced by a sublethal dose of proton irradiation.

The same effects were observed with rMnSOD short form.

Then rMnSOD long and short forms are useful for the treatment and/or prevention of damages induced by a sublethal dose of proton irradiation.

REFERENCES

Al-Gayyar M M, Eissa L A, Rabie A M, El. Gar A M (2007) Measurements of oxidative stress status and antioxidant activity in chronic leukemia patients. J Pharm Pharmacol 59: 409-17

Barbosa I A, Machado N G, Skildum A J, Scott P M, Oliveira P J (2012) Mitochondrial remodeling in cancer metabolism and survival: Potential for new therapies. Bioch Biophys Acta (BBA)—Reviews on Cancer 1826(1): 238-254, doi:10.1016/j.bbcan.2012.04.005

Battisti V, Maders L D, Bagatini M D, Santos K F, Spanevello R M, Maldonado P A, Brulé A O, Araújo Mdo C, Schetinger M R, Morsch V M (2008) Measurement of oxidative stress and antioxidant status in acute lymphoblastic leukemia patients. Clin Biochem 41(7-8): 511-8, doi:10.1016/j.clinbiochem.2008.01.027

Bassan R, Gatta G, Tondini C, Willemze R (2004) Adult acute lymphoblastic leukemia. Crit Rev Oncol Hematol 50: 223-261

Borrelli A, Antonietta Schiattarella, Roberto Mancini, Franco Morelli, Clemente Capasso, Viviana De Luca, Enrico Gori and Aldo Mancini Int. J. Cancer: 128, 453-459 (2011) The leader peptide of a human rec. MnSOD as molecular carrier which delivers high amounts of Cisplatin into tumor cells inducing a fast apoptosis in vitro Cooke M S, Evans M D, Dizdaroglu M, Lunec J (2003) Oxidative DNA damage: mechanisms, mutation, and disease. FASEB J 17(10): 1195-214, doi:10.1096/fj.02-0752rev Courtney K D, Corcoran R B, Engelman J A (2010) The PI3K pathway as drug target in human cancer. J Clin Oncol 28: 1075-83, doi:10.1200/JCO.2009.25.3641

De Luca A, Maiello R M, D'Alessio A, Pergameno M, Normanno N (2012) The RAS/RAF/MEK/ERK and the PI3K/AKT signaling pathways: role in cancer pathogenesis and implications for therapeutic approaches. Expert Opin Ther Targets 16(2): 17-27, doi: 10.1517/14728222.2011.639361

Fenolland J R, Giraud J M, May F, Mouinga A, Seck S & Renard J P, Evaluation de l'épaisseur choroïdienne par tomographie cohérence en optique (SD-OCT). Étude préliminaire dans le glaucome ouvert á angle. Journal Francais d'Ophtalmologie 34: 313-317 (2011)

Fujiwara T, et al., Enhanced depth imaging optical coherence tomography of the choroid in highly myopic eyes. Am J Ophthalmol 148: 445-450 (2009)

Goldenberg J M, Silverman L B, Levy D E, Dalton V K, Gelber R D, Lehmann L, Cohen H J, Sallan S E, Asselin B L (2003) Childhood T-cell acute lymphoblastic leukemia: the Dana-Farber Cancer Institute acute lymphoblastic leukemia consortium experience. J Clin Oncol 21: 3616-3622, doi: 10.1200/jco.2003.10.116

Hunter T, Bannister W H, Hunter G J (1997) Cloning, expression and characterization of two Manganese Superoxide Dismutase from Caenorhabditis elegans. J Biol Chem 272: 28652-28659, doi:10.1074/jbc.272.45.28652

Jan-Ling Hsu, et al., Silverman Catalytic Properties of Human Manganese Superoxide Dismutase JBC vol. 271: 30, July 26, p. 17687-17691, (1996)

Karuppiah Chockalingam, et al. Engineering and characterization of human manganese superoxide dismutase mutants with high activity and low product inhibition FEBS Journal Volume 273, Issue 21, pages 4853-4861, (2006).

Mainous A G III, Wells B J, Koopman R J, Everett C J, Gill J M (2005) Iron lipids, and risk of cancer in the Framingham Offspring cohort. Am J Epidemiol 161 (12): 1115-22, doi: 10.1093/aje/kwi131

Malyszczak K, Tomasz W, Mazur G, Lindner K, Pyszel A, Kiejna A, Kuliczkowski K, Andrzejak R (2005) Anxiety and depressive symptoms in patients treated due to haematologic malignancies. Psychiatr Pol 39(1): 33-40

Mancini A, Borrelli A, Schiattarella A, Fasano S, Occhiello A, Pica A, Sehr P, Tommasino M, Nuesch J P, Rommelaere J (2006) Tumor suppressive activity of variant isoform of manganese superoxide dismutase released by a human liposarcoma cell line. Int J Cancer 119: 932-43

Mancini A, Borrelli A, Schiattarella A, Aloj L, Aurilio M, Morelli F, Pica A, Occhiello A, Lorizio R, Mancini R, Sica A, Mazzarella L, Sica F, Grieco P, Novellino E, Pagnozzi D, Pucci P, Rommelaere J (2008) Biophysical and biochemical characterization of a liposarcoma-derived recombinant MnSOD protein acting as an anticancer agent. Int J Cancer 123: 2684-2695, doi: 10.1002/ijc.23791

Manda G, Nechifor M T, Neagu T M (2009) Reactive oxygen species, cancer and anti-cancer therapies. Curr Chem Biol 3: 342-366

Mashiba H, Matsunaga K (1988) Device for intracellular increase of oxygen free radicals and inhibition of MethA tumor cell proliferation: in vitro and in vivo studies. Int J Tissue React 10(5): 273-80

McCourt E A, et al., Measurement of sub-foveal choroidal thickness using spectral domain optical coherence tomography. Ophthalmic Surg Lasers Imaging 41: S28-S33 (2010)

McEligot A J, Yang S, Meyskens F (2005) Redox regulation by intrinsic species and extrinsic nutrients in normal and cancer cells. Annu Rev Nutr 25: 261-95, doi: 10.1146/annurev.nutr.25.050304.092633

Oltra A M, Carbonell F, Tormos C, Iradi A, Saez G T (2001) Antioxidant enzyme activities and production of MDA and 8-oxo-dg in chronic lymphocytic leukemia. Free Radic Biol Med 30: 1286-92

Pica A, Di Santi A, Basile F, Iacobellis F, Borrelli A, Schiattarella A, Mancini R, Mancini A (2010) Anti-Cancer, anti-Necrotic and Imaging Tumor Marker role of a novel form of Manganese Superoxide Dismutase and its leader peptide. Int J Biol Biomed Eng 4: 53-60

Spaide R F, Koizumi H & Pozzoni M C, Enhanced depth imaging spectral-domain optical coherence tomography. Am J Ophthalmol 146: 496-500 (2008)

Skarstein J, Aass N, Fossa S D, Skovlund E, Dahl A A (2000) Anxiety and depression in cancer patients: relation between the Hospital anxiety and depression scale and the European organization for Research and treatment of cancer core quality of life questionnaire. J Psychosom Res 49(1): 27-34

Schubbert S, Shannon K, Bollag G (2007) Hyperactive Ras in developmental disorders and cancer. Nat Rev Cancer 7: 295-308, doi:10.1038/nrc2109

Valko M, Rhodes C. J, Moncol J, Izakovic M, Mazur M (2006) Free radicals, metals and antioxidants in oxidative stress-induced cancer. Chem Biol Interact 160 (1): 1-40, doi:10.1016/j.cbi.2005.12.009.

Wan X S, Devalaraja M N, St Clair D K (1994) Molecular structure and organization of the human manganese superoxide dismutase gene. DNA. Cell Biol 13: 1127-1136, doi:10.1089/dna.1994.13.1127.

The invention claimed is:

1. A protein encoded by the nucleotide sequence of SEQ ID NO: 3.

2. The protein according to claim 1, produced by a process comprising expressing the nucleotide of SEQ ID NO: 3 in an *E. Coli* host cell.

3. A protein comprising the amino acid sequence of: SEQ ID NO: 4.

4. The protein according to claim 3, further comprising a TAG sequence.

5. A method for treating or diagnosing a disease characterized by an excess of free radicals, comprising administering an effective amount of the protein according to claim 1 to a patient in need thereof.

6. The method according to claim 5, wherein said disease belongs to the group consisting of vascular disease, including heart, coronary artery or peripheral vascular disease, dilated cardiomyopathy, aneurism, cancer, chronic obstructive pulmonary disease or COPD, dementia, and neurodegenerative disorders, aging, diabetes, autoimmune disorders with rheumatoid arthritis, ocular disease, a disease of the retina or of the crystalline lens, cataract, liver cirrhosis, and non-alcoholic steatohepatitis (NASH).

7. A method for treating a neuroinflammatory disease, comprising administering an effective amount of the protein according to claim 1 to a patient in need thereof.

8. The method according to claim 7, wherein the neuroinflammatory disease is a neurodegenerative disease.

9. The method according to claim 8, wherein the neurodegenerative disease is selected from the group consisting of: Alzheimer's disease, Parkinson disease, Multiple Sclerosis, Depression, Basal Ganglia diseases, Atherosclerosis, Stroke, Trauma, Substance use disorders, Amyotrophic Lateral Sclerosis, and Mitochondrial Encephalopathies.

10. A method for treating or diagnosing a tumor pathology, either alone or in combination, as enhancer, with other therapies, comprising administering an effective amount of the protein according to claim 1 to a patient in need thereof.

11. The method according to claim 10, wherein the tumor pathology is a leukemia.

12. The method according to claim 10, wherein the tumor pathology is a neuroblastoma.

13. A method for treating cataracts, comprising administering an effective amount of the protein according to claim 1 to a patient in need thereof.

14. A method of treating damage induced by a sublethal dose of proton irradiation, comprising administering an effective amount of the protein according to claim 1 to a patient in need thereof.

15. A nucleotide sequence coding for the protein as defined in claim 3.

16. A vector able to efficiently express the protein as defined in claim 3, wherein the vector comprises the nucleotide sequence of SEQ ID NO: 3.

17. A host cell engineered with the vector according to claim 16.

18. A pharmaceutical composition comprising the protein according to claim 1, and suitable excipients, diluents and/or carriers.

19. A kit for the diagnosis of a tumor disease comprising the protein according to claim 1.

20. The method according to claim 11, wherein the leukemia is acute lymphoblastic leukemia.

21. A method of producing the protein according to claim 3, comprising culturing a host cell expressing the nucleotide sequence of SEQ ID NO: 3, and purifying the produced protein comprising the sequence of SEQ ID NO: 4.

* * * * *